(12) United States Patent
Forsell

(10) Patent No.: US 10,098,744 B2
(45) Date of Patent: Oct. 16, 2018

(54) JOINT DEVICE AND METHOD

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 0 days.

(21) Appl. No.: 15/193,184

(22) Filed: Jun. 27, 2016

(65) Prior Publication Data

US 2016/0302931 A1 Oct. 20, 2016

Related U.S. Application Data

(63) Continuation of application No. 13/383,293, filed as application No. PCT/SE2010/050819 on Jul. 12, 2010, now Pat. No. 9,375,315.
(Continued)

(30) Foreign Application Priority Data

| Jul. 10, 2009 | (SE) | 0900957 |
| Jul. 10, 2009 | (SE) | 0900958 |
| Jul. 10, 2009 | (SE) | 0900959 |
| Jul. 10, 2009 | (SE) | 0900960 |
| Jul. 10, 2009 | (SE) | 0900961 |

(Continued)

(51) Int. Cl.
*A61F 2/30* (2006.01)
*A61B 17/16* (2006.01)
(Continued)

(52) U.S. Cl.
CPC ...... *A61F 2/30756* (2013.01); *A61B 17/1666* (2013.01); *A61F 2/30* (2013.01);
(Continued)

(58) Field of Classification Search
CPC .... A61F 2/30756; A61F 2/30; A61F 2/30721; A61F 2/32; A61F 2/34; A61B 17/1666
(Continued)

(56) References Cited

U.S. PATENT DOCUMENTS

| 2004/0236424 A1* | 11/2004 | Berez | A61B 5/1076 623/14.12 |
| 2005/0059964 A1* | 3/2005 | Fitz | A61B 18/1477 606/41 |

(Continued)

OTHER PUBLICATIONS

"Knee Arthroscopic Surgery" (http://www.surgeryencyclopedia.com, published May 25, 2008, last accessed via Internet Archive Wayback Machine on Jun. 10, 2017.*

*Primary Examiner* — Joseph S Del Sole
*Assistant Examiner* — Lawrence D. Hohenbrink, Jr.

(57) ABSTRACT

A mold adapted to be introduced into a joint of a human patient for resurfacing at least one carrying contacting surface of said joint is provided. The mold is adapted to receive material for resurfacing at least one carrying contacting surface of said joint. The mold is further adapted to be resorbed by the human body or melt after having served its purpose.

Further, a method of treating hip joint osteoarthritis in a human patient by providing an artificial hip joint surface using a mold is provided. The method comprises the steps of: said mold being placed inside of said hip joint, said mold being injected with a fluid adapted to harden, said fluid hardening inside of said hip joint, said mold being resorbed by the human body, and said hardened fluid serving as artificial hip joint surface.

13 Claims, 16 Drawing Sheets

Related U.S. Application Data

(60) Provisional application No. 61/229,752, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,789, filed on Jul. 30, 2009, provisional application No. 61/229,796, filed on Jul. 30, 2009, provisional application No. 61/229,735, filed on Jul. 30, 2009, provisional application No. 61/229,738, filed on Jul. 30, 2009, provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,730, filed on Jul. 30, 2009, provisional application No. 61/229,731, filed on Jul. 30, 2009, provisional application No. 61/229,733, filed on Jul. 30, 2009, provisional application No. 61/229,802, filed on Jul. 30, 2009, provisional application No. 61/229,805, filed on Jul. 30, 2009, provisional application No. 61/229,811, filed on Jul. 30, 2009, provisional application No. 61/229,815, filed on Jul. 30, 2009, provisional application No. 61/229,816, filed on Jul. 30, 2009, provisional application No. 61/229,755, filed on Jul. 30, 2009.

(30) Foreign Application Priority Data

| Jul. 10, 2009 | (SE) | 0900962 |
| Jul. 10, 2009 | (SE) | 0900963 |
| Jul. 10, 2009 | (SE) | 0900964 |
| Jul. 10, 2009 | (SE) | 0900965 |
| Jul. 10, 2009 | (SE) | 0900967 |
| Jul. 10, 2009 | (SE) | 0900969 |
| Jul. 10, 2009 | (SE) | 0900970 |
| Jul. 10, 2009 | (SE) | 0900971 |
| Jul. 10, 2009 | (SE) | 0900972 |
| Jul. 10, 2009 | (SE) | 0900973 |
| Jul. 10, 2009 | (SE) | 0900974 |
| Jul. 10, 2009 | (SE) | 0900975 |
| Jul. 10, 2009 | (SE) | 0900976 |
| Jul. 10, 2009 | (SE) | 0900977 |
| Jul. 10, 2009 | (SE) | 0900978 |
| Jul. 10, 2009 | (SE) | 0900979 |
| Jul. 10, 2009 | (SE) | 0900980 |
| Jul. 10, 2009 | (SE) | 0900981 |
| Jul. 30, 2009 | (SE) | 0900966 |
| Jul. 30, 2009 | (SE) | 0900968 |
| Nov. 24, 2009 | (WO) | PCT/SE2009/000502 |

(51) Int. Cl.

| *A61F 2/32* | (2006.01) |
| *A61F 2/34* | (2006.01) |
| *A61B 17/56* | (2006.01) |
| *A61B 17/74* | (2006.01) |
| *A61B 17/86* | (2006.01) |
| *A61F 2/36* | (2006.01) |
| *A61F 2/46* | (2006.01) |
| *A61F 2/48* | (2006.01) |
| *A61M 5/142* | (2006.01) |
| *A61B 17/88* | (2006.01) |
| *A61B 18/04* | (2006.01) |
| *A61F 2/38* | (2006.01) |
| *A61L 27/16* | (2006.01) |
| *A61L 31/04* | (2006.01) |
| *A61L 31/14* | (2006.01) |

(52) U.S. Cl.
CPC ............ *A61F 2/30721* (2013.01); *A61F 2/32* (2013.01); *A61F 2/34* (2013.01); *A61B 17/1604* (2013.01); *A61B 17/1637* (2013.01); *A61B 17/1664* (2013.01); *A61B 17/1668* (2013.01); *A61B 17/562* (2013.01); *A61B 17/74* (2013.01); *A61B 17/86* (2013.01); *A61B 17/8805* (2013.01); *A61B 18/04* (2013.01); *A61B 2018/046* (2013.01); *A61F 2/30942* (2013.01); *A61F 2/36* (2013.01); *A61F 2/3601* (2013.01); *A61F 2/3603* (2013.01); *A61F 2/389* (2013.01); *A61F 2/3859* (2013.01); *A61F 2/46* (2013.01); *A61F 2/4618* (2013.01); *A61F 2002/30065* (2013.01); *A61F 2002/3067* (2013.01); *A61F 2002/30471* (2013.01); *A61F 2002/30507* (2013.01); *A61F 2002/30558* (2013.01); *A61F 2002/30563* (2013.01); *A61F 2002/30565* (2013.01); *A61F 2002/30579* (2013.01); *A61F 2002/30583* (2013.01); *A61F 2002/30668* (2013.01); *A61F 2002/30672* (2013.01); *A61F 2002/30673* (2013.01); *A61F 2002/30675* (2013.01); *A61F 2002/30754* (2013.01); *A61F 2002/30757* (2013.01); *A61F 2002/30759* (2013.01); *A61F 2002/30878* (2013.01); *A61F 2002/30886* (2013.01); *A61F 2002/3241* (2013.01); *A61F 2002/3483* (2013.01); *A61F 2002/3496* (2013.01); *A61F 2002/3615* (2013.01); *A61F 2002/3631* (2013.01); *A61F 2002/4631* (2013.01); *A61F 2002/4635* (2013.01); *A61F 2002/4655* (2013.01); *A61F 2002/4677* (2013.01); *A61F 2002/482* (2013.01); *A61F 2002/485* (2013.01); *A61F 2250/00* (2013.01); *A61L 27/16* (2013.01); *A61L 31/042* (2013.01); *A61L 31/044* (2013.01); *A61L 31/046* (2013.01); *A61L 31/148* (2013.01); *A61L 2300/406* (2013.01); *A61L 2400/06* (2013.01); *A61L 2430/24* (2013.01); *A61M 5/14276* (2013.01); *A61M 2005/14284* (2013.01)

(58) Field of Classification Search
USPC .................. 249/61; 264/221, 222, 313, 317; 156/155; 425/2, 175, 176, DIG. 2
See application file for complete search history.

(56) References Cited

U.S. PATENT DOCUMENTS

| 2008/0234820 | A1* | 9/2008 | Felt | A61B 17/562 623/14.12 |
| 2008/0306574 | A1* | 12/2008 | Ravussin | A61B 18/24 607/89 |
| 2009/0043344 | A1* | 2/2009 | Schlotterback | A61F 2/30756 606/86 R |

* cited by examiner

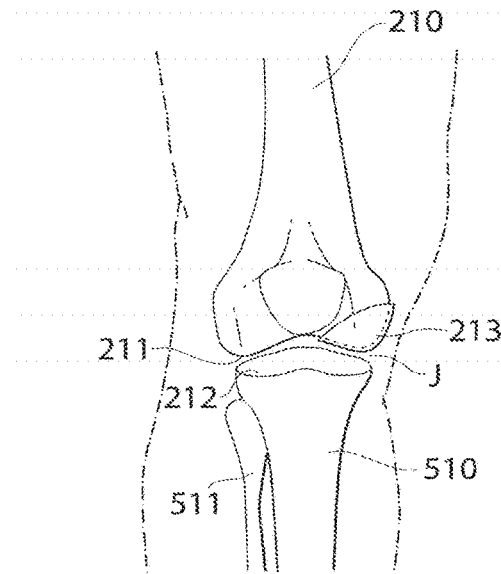
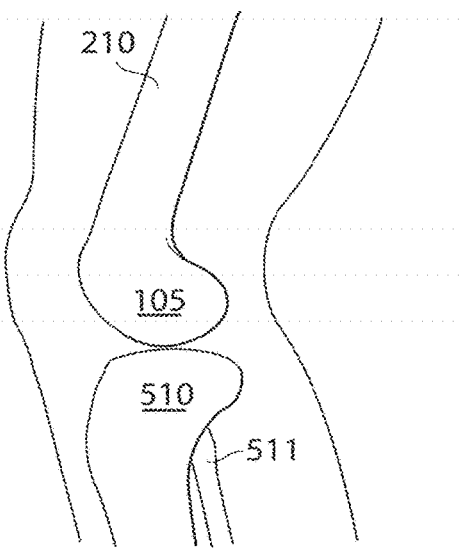
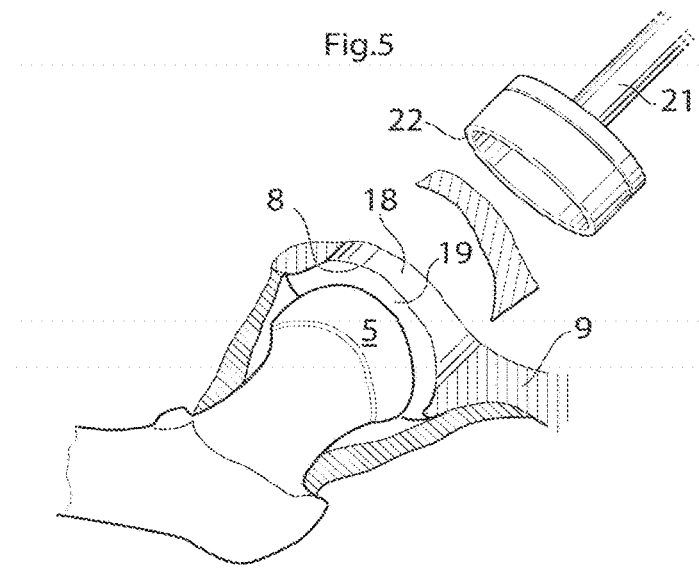
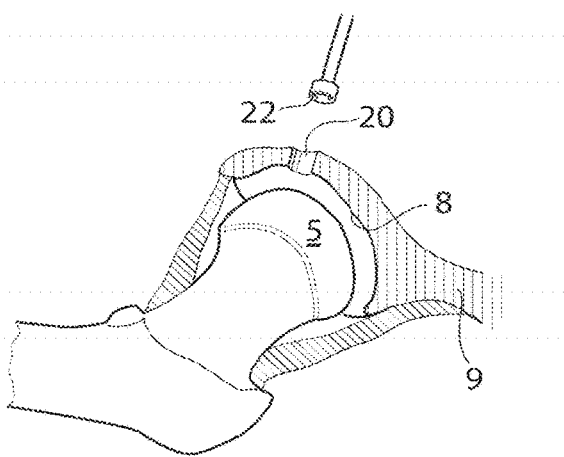

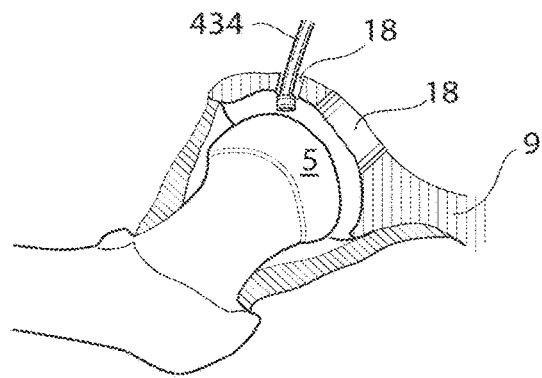
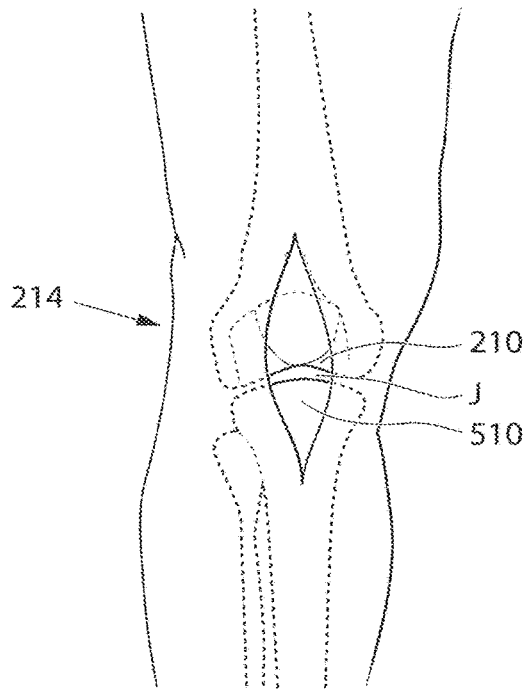
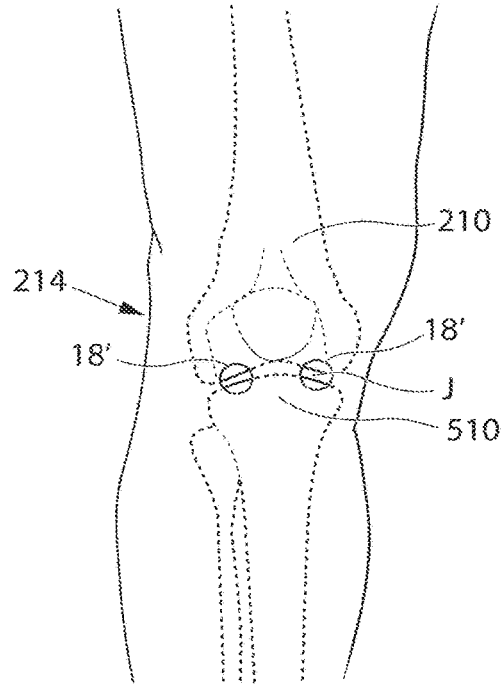

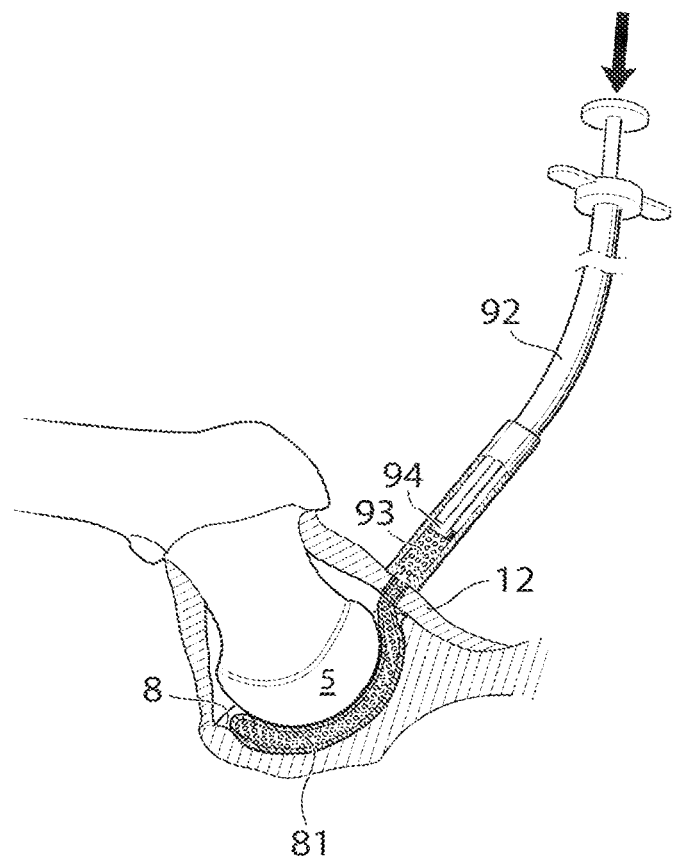
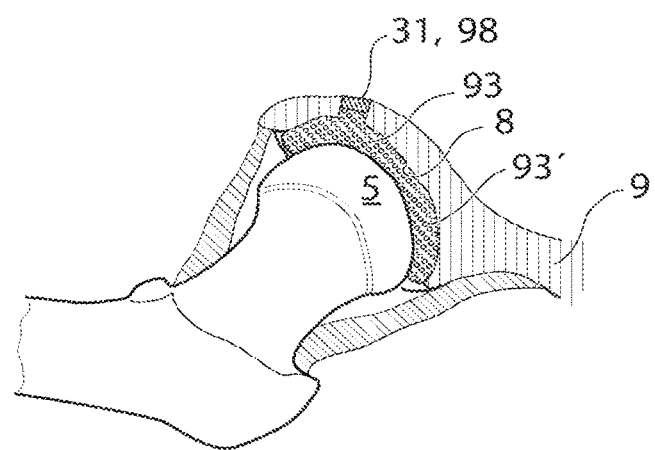
Fig. 24

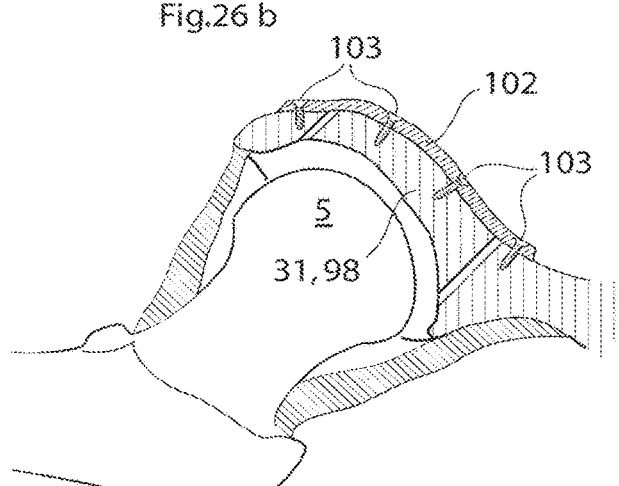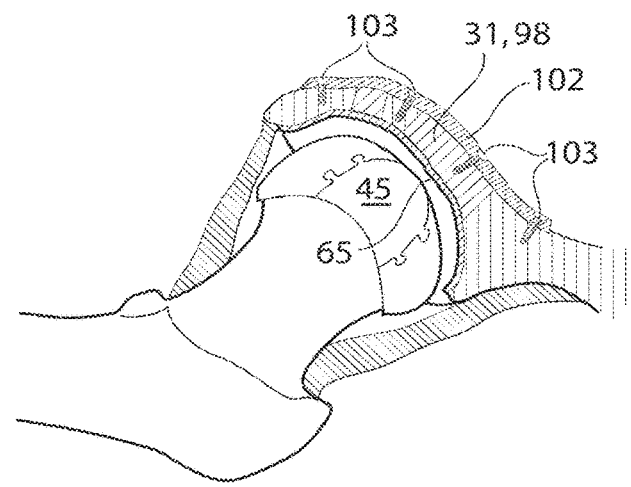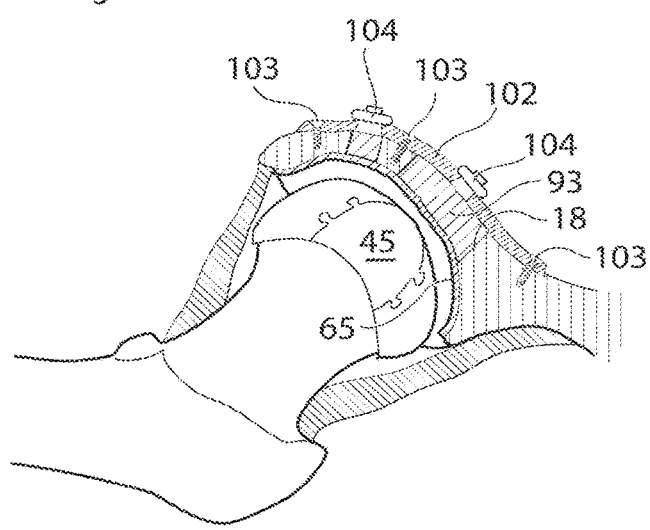

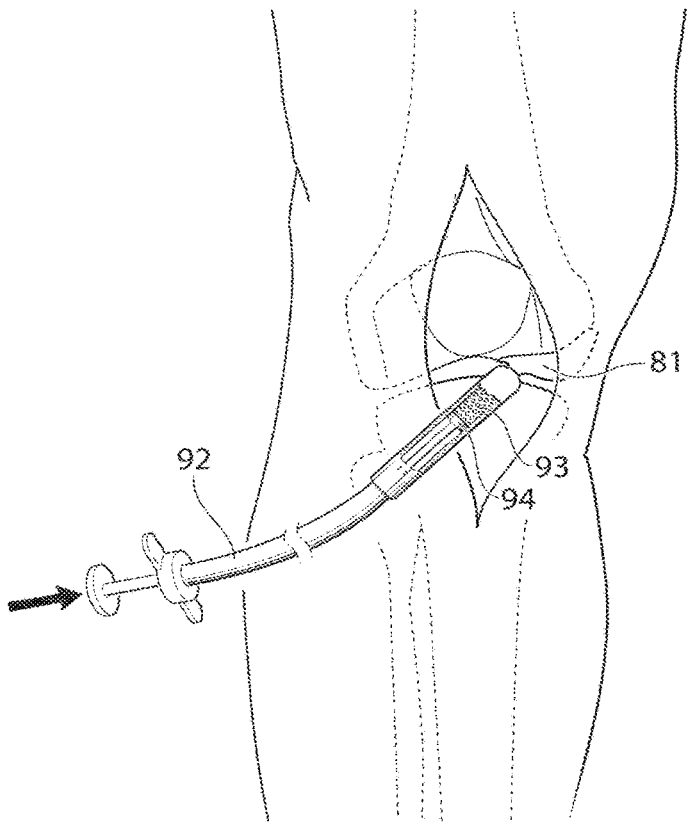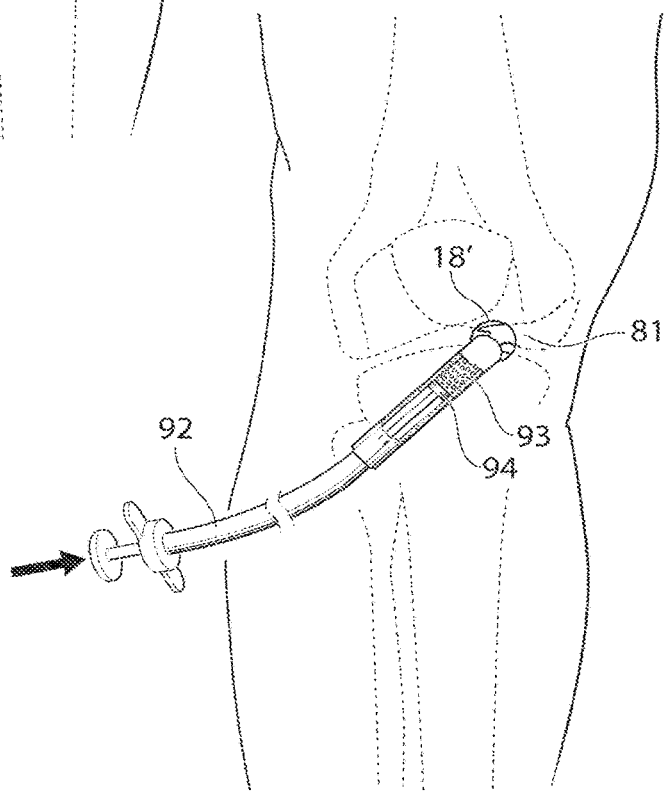

JOINT DEVICE AND METHOD

This application is a continuation of U.S. application Ser. No. 13/383,293, filed on 10 Jan. 2012, which is the U.S. national phase of International Application No. PCT/SE2010/050819, filed 12 Jul. 2010, which designated the U.S. and claims the benefit of U.S Provisional Nos. 61/229,730 filed 30 Jul. 2009; 61/229,731 filed 30 Jul. 2009; 61/229,733 filed 30 Jul. 2009; 61/229,735 filed 30 Jul. 2009; 61/229,738 filed 30 Jul. 2009; 61/229,739 filed 30 Jul. 2009; 61/229,743 filed 30 Jul. 2009; 61/229,745 filed 30 Jul. 2009; 61/229,746 filed 30 Jul. 2009; 61/229,747 filed 30 Jul. 2009; 61/229,748 filed 30 Jul. 2009; 61/229,751 filed 30 Jul. 2009; 61/229,752 filed 30 Jul. 2009; 61/229,755, filed 30 Jul. 2009; 61/229,761 filed 30 Jul. 2009; 61/229,767 filed 30 Jul. 2009; 61/229,778 filed 30 Jul. 2009; 61/229,786 filed 30 Jul. 2009; 61/229,789 filed 30 Jul. 2009; 61/229,796 filed 30 Jul. 2009; 61/229,802 filed 30 Jul. 2009; 61/229,805 filed 30 Jul. 2009; 61/229,811 filed 30 Jul. 2009; 61/229,815 filed 30 Jul. 2009; 61/229,816 filed 30 Jul. 2009; and which claims priority to Swedish Application Nos.: 0900981-2 filed 10 Jul. 2009; 0900957-2 filed 10 Jul. 2009; 0900958-0 filed 10 Jul. 2009; 0900959-8 filed 10 Jul. 2009; 0900960-6 filed 10 Jul. 2009; 0900961-4 filed 10 Jul. 2009; 0900962-2 filed 10 Jul. 2009; 0900963-0 filed 10 Jul. 2009; 0900964-8 filed 10 Jul. 2009; 0900965-5 filed 10 Jul. 2009; 0900966-3 filed 10 Jul. 2009; 0900967-1 filed 10 Jul. 2009; 0900968-9 filed 10 Jul. 2009; 0900969-7 filed 10 Jul. 2009; 0900970-5 filed 10 Jul. 2009; 0900971-3 filed 10 Jul. 2009; 0900972-1 filed 10 Jul. 2009; 0900973-9 filed 10 Jul. 2009; 0900974-7 filed 10 Jul. 2009; 0900975-4 filed 10 Jul. 2009; 0900976-2 filed 10 Jul. 2009; 0900977-0 filed 10 Jul. 2009; 0900978-8 filed 10 Jul. 2009; 0900979-6 filed 10 Jul. 2009; 0900980-4 filed 10 Jul. 2009 and PCT/SE2009/000502 filed 24 Nov. 2009, the entire contents of each of which are hereby incorporated by reference.

FIELD OF INVENTION

The present invention relates generally to a medical device for implantation in a joint, and a method of providing said medical device.

BACKGROUND

Joint osteoarthritis is a syndrome in which low-grade inflammation results in pain in the joints, caused by abnormal wearing of the cartilage that acts as a cushion inside if the joint. This abnormal wearing of the cartilage also results in a decrease of the joints lubricating fluid called synovial fluid. Joint osteoarthritis is estimated to affect 80% of all people over 65 years of age, in more or less serious forms.

The present treatment for joint osteoarthritis comprises NSAID drugs, local injections of hyaluronic acid or glucocorticoid to help lubricating the joint, and replacing parts of the joint with a prosthesis through orthopedic surgery.

The replacing of parts of the joint is one of the most common surgeries to date performed at hundreds of thousands of patients in the world every year. The most common method comprises placing a metal prosthesis in Femur and a plastic bowl in acetabulum. This operation is usually done through a lateral incision in the hip and upper thigh and through, fascia lata and the lateral muscles of the thigh. To get access to the hip joint, the supporting hip joint capsule attached to femur and Ilium of pelvis needs to be penetrated, making it difficult to get a fully functional joint after the surgery. Femur is then cut at the neck with a bone saw and the prosthesis is placed in femur either with bone cement or without. Acetabulum is slightly enlarged using an acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

Conventional orthopedic surgery has drawbacks in that it is highly invasive, which damages the ligaments, tendons and surrounding tissue such that they are weakened. Some of the ligaments surrounding the joints, such as the ligaments of the hip and knee joint capsules never fully regain their strength once they are severed, resulting in the patient getting a limited motion range and/or load carrying capability. The large incisions are needed since the prosthetic parts usually are of considerable size and needs to be placed in contact with the joint through the incision. Making a large incision creates a large surface exposed to the threat of bacterial and/or viral infections and extends the needed hospital stay.

SUMMARY

A mould adapted to be introduced into a joint of a human patient for resurfacing at least one carrying contacting surface of the joint is provided. The mould is adapted to receive material for resurfacing at least one carrying contacting surface of the joint. The mould comprises a mould material adapted to be affected by a fluid injected into said mould such that said mould melts or is resorbed by the human body after having served its purpose.

According to one embodiment the mould comprises a hyaluronan-based material, in which case the mould could be adapted to receive hyaluronidase, and wherein the material of said mould is affected by the injection of the hyaluronidase such that the mould melts or is resorbed faster than without the injection of the hyaluronidase.

According to one embodiment the mould comprises a fibrin-based material, in which case the mould could be adapted to receive plasmin, and wherein the material of said mould is affected by the injection of the plasmin such that the mould melts or is resorbed faster than without the injection of the plasmin.

According to one embodiment the mould comprises a collagen-based material, in which case the mould could be adapted to receive collagenase, and wherein the material of said mould is affected by the injection of the collagenase such that the mould melts or is resorbed faster than without the injection of the collagenase.

According to one embodiment the mould comprises a chitosan-based material, in which case the mould could be adapted to receive lysozyme, and wherein the material of said mould is affected by the injection of the lysozyme such that the mould melts or is resorbed faster than without the injection of the lysozyme.

In any of the embodiment herein, the mould material could be adapted to be melted by the temperature of the received material.

The received material could in any of the embodiment herein comprise at least one material selected from the group consisting of: polytetrafluoroethylene, perfluoroalkoxy, fluorinated ethylene propylene, polyethylene, and acrylic polymer mixed with alumina trihydrate.

According to one embodiment, the mould could be adapted to be melted by the received material having a temperature in the interval 40-60 degrees Celsius, or in the interval 60-90 degrees Celsius, or in the interval 90-200 degrees Celsius, or in the interval 200-400 degrees Celsius or more than 400 degrees Celsius.

According to yet another embodiment, the mould could be collapsible such that said mould can be introduced into the hip joint through a hole in any of: the pelvic bone, the femoral bone and the hip joint capsule.

According to yet another embodiment, the mould could be collapsible such that said mould can be introduced into the knee joint through a hole in any of: the femoral bone, the tibia bone and the knee joint capsule.

The mould according to any one of the embodiments could further comprise an injecting entrance in said mould adapted to receive injected material into said mould.

A mould adapted to be introduced into a joint of a human patient for resurfacing at least one carrying contacting surface of the joint is further provided. The mould is adapted to receive material for resurfacing at least one carrying contacting surface of the joint. The mould comprises a first material adapted to enclose a second material injected into said mould, the first and said second material is the same material, such that the first and said second material forms a substantially homogenous material for resurfacing at least one carrying contacting surface of the joint.

The mould could according to one embodiment be collapsible such that the mould can be introduced into the hip joint through a hole in any of: the pelvic bone, the femoral bone and the hip joint capsule.

According to yet another embodiment, the mould could be collapsible such that the mould can be introduced into the knee joint through a hole in any of: the femoral bone, the tibia bone and the knee joint capsule.

The mould could further comprising an injecting entrance in said mould adapted to receive injected material into said mould.

The first and second material in any of the embodiments could comprise a material selected from the group consisting of: polytetrafluoroethylene, perfluoroalkoxy, fluorinated ethylene propylene, polyethylene, and acrylic polymer mixed with alumina trihydrate.

A system comprising the mould according to any one of the preceding embodiments, and an injecting member in connection with said mould, adapted to inject a fluid into said mould is further provided.

The injecting member comprises at least one container, a fluid conduit, and a fluid injecting element adapted to be in connection with said mould.

According to one embodiment, the fluid injecting member could comprise two containers, and wherein the first and the second containers could be adapted to hold different fluids.

According to yet another embodiment, the injecting member further comprises a mixing unit adapted to mix said fluids contained in said two containers.

According to yet another embodiment, the system further comprises at least two different fluids each adapted to be contained within one of said two containers, wherein one of said two fluids is adapted to act as catalyzing agent.

The system could further comprises a fluid adapted to be injected into said mould, wherein said fluid is adapted to cure and change from a fluid to fixed form. The fluid could be adapted to be cured by UV-light or by a gas serving as catalyzing agent.

The injecting member could according to one embodiment comprise at least one bent portion, which could be bent at an adjustable angle.

According to yet another embodiment, the system could further comprise a heating element adapted to heat said container for heating the fluid contained therein.

According to yet another embodiment, the heating element could be adapted to heat the fluid to a temperature in the interval 40-60 degrees Celsius, or in the interval 60-90 degrees Celsius, or in the interval 90-200 degrees Celsius, or in the interval 200-400 degrees Celsius or more than 400 degrees Celsius.

According to yet another embodiment, the system further comprises a radiation source adapted to radiate said container for sterilizing the fluid contained therein.

According to yet another embodiment, the fluid comprises at least one antibacterial substance, wherein said material adapted to be injected into said mould is held sterile by said at least one antibacterial substance. In other embodiments, the container has antibacterial inner surfaces, adapted to be in contact with said fluid.

In any of the embodiments herein, the device or system could be adapted to receive a fluid material having a melting point in the interval 40-60 degrees Celsius, or in the interval 60-90 degrees Celsius, or in the interval 90-200 degrees Celsius, or in the interval 200-400 degrees Celsius or more than 400 degrees Celsius.

The fluid in any of the embodiments herein could comprise at least one material selected from the group consisting of: polytetrafluoroethylene, perfluoroalkoxy, fluorinated ethylene propylene, polyethylene, and acrylic polymer mixed with alumina trihydrate.

A medical device for providing a joint surface is further provided. The medical device could comprise a mould adapted to be introduced into a joint of the patient, and a material adapted to cure within said mould for resurfacing at least one carrying contacting surface of the joint. The mould could comprise a mould material adapted to be affected by the material adapted to cure within said mould, such that said mould melts or is resorbed by the human body after having served its purpose.

The medical device could be adapted for resurfacing at least one of: the hip joint caput femur surface, the hip joint acetabulum surface, the femoral knee joint surface, and the tibia knee joint surface. The material adapted to cure could comprise at least one material selected from the group consisting of: polytetrafluoroethylene, perfluoroalkoxy, fluorinated ethylene propylene, polyethylene, and acrylic polymer mixed with alumina trihydrate.

A method of providing an artificial hip joint surface using a mould is further provided. The method comprises the steps of: the mould being placed inside of the hip joint, the mould being injected with a fluid adapted to cure, the fluid curing inside of the hip joint, the mould being affected by a fluid injected into said mould, the mould being resorbed by the human body or melted by the injected material, and the fluid adapted to cure serving as artificial hip joint surface.

A method of providing an artificial knee joint surface using a mould is further provided, the method comprises the steps of: the mould being placed inside of the knee joint, the mould being injected with a fluid adapted to cure, the fluid curing inside of the knee joint, the mould being affected by a fluid injected into said mould, the mould being resorbed by the human body or melted by the injected material, and the fluid adapted to cure serving as artificial knee joint surface.

The methods could further comprise the step of heating said fluid to a temperature of more than 40 degrees Celsius for transforming said fluid from a solid to a fluid, and said injected fluid transforming to a solid when received in said mould, or heating said fluid to a temperature of more than 60 degrees Celsius for transforming said fluid from a solid to a fluid, and said injected fluid transforming to a solid when received in said mould, or heating said fluid to a temperature of more than 90 degrees Celsius for transforming said fluid from a solid to a fluid, and said injected fluid transforming to a solid when received in said mould, or heating said material to a temperature of more than 200 degrees Celsius for transforming said material into a fluid, or heating said fluid to a temperature of more than 400 degrees Celsius for transforming said fluid from a solid to a fluid, and said injected fluid transforming to a solid when received in said mould.

According to one embodiment, the step of placing the mould into the hip joint comprises the step of introducing the mould through a hole in the pelvic bone or a hole in the femoral bone or a hole in the hip joint capsule. Or the step of placing said mould into the knee joint comprises the step of introducing said mould through a hole in the femoral bone or a hole in the tibia bone or a hole in the knee joint capsule.

A method for treating hip joint osteoarthritis in a human patient by providing at least one hip joint surface is further provided. The hip joint comprises a caput femur and an acetabulum. The method comprising the steps of: cutting the skin of the human patient, dissecting an area of the pelvic bone on the opposite side from the acetabulum, creating a hole in said dissected area, said hole passing through the pelvic bone and into the hip joint of the human patient, placing a mould between the acetabulum and the caput femur, and injecting material into said mould for providing at least one hip joint surface.

The mould could be resorbable or adapted to melt by the material being heated.

According to one embodiment, the step of cutting the skin of the human patient could be performed in the abdominal wall of the human patient. According to another embodiment, the step of dissecting an area of the pelvic bone comprises dissecting in at least one of the following areas: the abdominal cavity, an area between peritoneum and the pelvic bone, the pelvic area, and the inguinal area.

A method for resurfacing at least one carrying contacting surface of a hip joint of a human patient is further provided. The hip joint comprising an acetabulum and a caput femur having contacting carrying surfaces carrying weight in the hip joint, the method comprising the steps of: inserting a needle or a tube like instrument into the patient's hip joint, using the needle or tube like instrument to fill the hip joint with a fluid, placing at least one arthroscopic camera and at least one instrument in the patient's hip joint, introducing a mould passing into the hip joint, placing a mould between the acetabulum and the caput femur, and said mould being injected with a fluid adapted to cure, said fluid curing inside of the hip joint, said mould being affected by a fluid injected into said mould, said mould being resorbed by the human body or melted by the injected material, and said fluid adapted to cure serving as artificial hip joint surface.

A method for resurfacing at least one carrying contacting surface of a hip joint of a human patient is further provided, the hip joint comprising an acetabulum and a caput femur having contacting carrying surfaces carrying weight in the hip joint, the method comprising the steps of: inserting a needle or a tube like instrument into the patient's abdomen, using the needle or tube like instrument to fill the abdomen with a gas, placing at least two laparoscopic trocars in the patient's abdomen, inserting a camera through one of the laparoscopic trocars into the patient's abdomen, inserting at least one dissecting tool through one of said at least two laparoscopic trocars, dissecting an area of the pelvic bone on the opposite side from the acetabulum, creating a hole in said dissected area, said hole passing through the pelvic bone and into the hip joint of the human patient, introducing a mould passing into the hip joint, placing said mould between the acetabulum and the caput femur, the mould being injected with a fluid adapted to cure, said fluid curing inside of the hip joint, said mould being affected by a fluid injected into said mould, said mould being resorbed by the human body or melted by the injected material, and said fluid adapted to cure serving as artificial hip joint surface.

A method for resurfacing at least one carrying contacting surface of a knee joint of a human patient is further provided. The knee joint comprises the femoral bone and the tibia bone having contacting carrying surfaces carrying weight in the knee joint, the method comprising the steps of: inserting a needle or a tube like instrument into the patient's knee joint, using the needle or tube like instrument to fill the knee joint with a fluid, placing at least one arthroscopic camera and at least one instrument in the patient's knee joint, introducing a mould passing into the knee joint, placing a mould between the femoral bone and the tibia bone, injecting said mould with a fluid adapted to cure, said fluid curing inside of the hip joint, said mould being affected by a fluid injected into said mould, said mould being resorbed by the human body or melted by the injected material, and said fluid adapted to cure serving as artificial hip joint surface.

A method for resurfacing at least one carrying contacting surface of a knee joint of a human patient is further provided. The knee joint comprises the femoral bone and the tibia bone having contacting carrying surfaces carrying weight in the knee joint, the method comprises the steps of: inserting a needle or a tube like instrument into the patient's knee joint, using the needle or tube like instrument to fill the knee joint with a gas, placing at least one arthroscopic camera and at least one surgical instrument in the patient's knee joint, dissecting an area of the tibia bone, creating a hole in said dissected area, said hole passing through the tibia bone and into the knee joint of the human patient, introducing a mould through said hole passing into the knee joint, placing said mould between the femoral bone and the tibia bone, injecting said mould with a fluid adapted to cure, said fluid curing inside of the knee joint, said mould being affected by a fluid injected into said mould, said mould being resorbed by the human body or melted by the injected material, and said fluid adapted to cure serving as artificial knee joint surface.

Another object is to provide a mould adapted to be introduced into a joint of a human patient for resurfacing carrying contacting surfaces of said joint. The mould is adapted to receive material for resurfacing the carrying contacting surfaces of the joint. Furthermore the mould is adapted to be resorbed by the human body or melt after having served its purpose. The injecting of a material enables a less invasive procedure of resurfacing carrying contacting surfaces of said joint.

According to one embodiment the mould further comprises an injecting member in connection with the mould and adapted to inject material into the mould.

According to one embodiment the mould is adapted to be introduced into the hip joint through a hole. The hole could be placed in at least one if: the pelvic bone, the femoral bone and the hip joint capsule.

According to one embodiment the mould according to any of the embodiments above comprises a biocompatible material adapted to be resorbed by the human body, such as a collagen type of substance. According to other embodiments the biocompatible material is adapted to be melted by the injected substance.

The mould according to any of the embodiments herein could further comprise an injecting entrance in said mould being adapted to receive injected material into the mould.

Injecting Member

According to one embodiment the mould comprises injecting member adapted to inject material into a mould. The injecting member could comprise at least one container, a material injecting member in connection with the mould and a material driving member in connection with the material injecting member.

According to one embodiment the injecting member adapted to inject material into the mould, further comprises a second container. The first and second containers could be adapted to hold different fluids. In the embodiment where the injecting member comprises a second container it is conceivable that the injecting member further comprises a mixing unit adapted to mix the fluids contained in said two containers.

The fluid is preferably adapted to harden after the injecting into the mould, either on its own or by use of a catalyzing agent. In the case where the injecting member comprises two different fluids, one of the fluids could be adapted to act as catalyzing agent. It is furthermore conceivable that the material or fluid is adapted to harden using UV-light, radiation, catalysing gas or thermal change.

System

A second aspect is a system for treating osteoarthritis in a hip joint. The system comprises a mould adapted to be introduced into a joint of a human patient for resurfacing at least one carrying contacting surface of the hip joint. The mould is adapted to receive material for resurfacing at least one carrying contacting surface of the hip joint, and the mould is adapted to be resorbed by the human body or melt after having served its purpose. The system also comprises an injecting member in connection with the mould and adapted to inject material into the mould. According to another embodiment the injecting member adapted to inject material into the mould is further adapted to be bent. The injecting member could be bent using a fixed angle, an adjustable angle, a parallel displaced part or section, or a flexible part or section.

The fluid or material adapted to be injected into the mould in the hip or knee joint is preferably kept sterile. This could be done by means of heat, radiation, antibacterial substances, or antibacterial surfaces. The mould could be adapted to be introduced into the knee joint through a hole in the femoral bone, into the knee joint through a hole in the tibia bone or into the knee joint through a hole in the knee joint capsule.

The mould according to any of the embodiments herein could further be adapted to be resorbed by the human body within one to six months or substantially resorbed by the human body within 6-8 weeks.

According to one embodiment the mould is adapted to be melted at 40 degrees Celsius or higher, according to a second embodiment the mould is adapted to be melted at 60 degrees Celsius or higher, according to a third embodiment the mould is adapted to be melted at 90 degrees Celsius or higher, according to a fourth embodiment the mould is adapted to be melted at 200 degrees Celsius or higher, and according to a fifth embodiment the mould is adapted to be melted at 400 degrees Celsius or higher.

According to one embodiment the system is adapted to be used in connection with the hip joint, and in another embodiment the system is adapted to be used in connection with the knee joint.

According to one embodiment the material is adapted to be injected as a fluid and further adapted to become fixed form, when received into the mould, and the material becomes a fluid at a temperature of more than 40 degrees Celsius. According to yet another embodiment the material becomes fluid at a temperature of more than 60 degrees Celsius. According to yet another embodiment the material becomes fluid at a temperature of more than 90 degrees Celsius. According to yet another embodiment the material becomes fluid at a temperature of more than 200 degrees Celsius. According to yet another embodiment the material becomes fluid at a temperature of more than 400 degrees Celsius.

The medical device according to any of the embodiments could comprise at least one material selected from a group consisting of: polytetrafluoroethylene, perfluoroalkoxy and fluorinated ethylene propylene. It is furthermore conceivable that the material comprises a metal alloy, such as cobolt-chromium or titanium or stainless steel, or polyethylene, such as crosslinked polyethene or gas sterilized polyethene. The use of ceramic material is also conceivable, in the contacting surfaces or the entire medical device such as zirconium ceramics or alumina ceramics. According to one embodiment the medical device comprises a hydroxy-apatite coating.

In other embodiments the medical device could comprise fluoropolymer resins, Kevlar and/or acrylic polymer mixed with alumina trihydrate.

Method

A method for resurfacing at least one carrying contacting surface of a knee joint of a human patient is further provided. The knee joint comprising the femoral bone and the tibia bone having contacting carrying surfaces carrying weight in the knee joint, the method comprises the steps of: creating a hole passing into the knee joint, placing a mould between the femoral bone and the tibia bone, and injecting material into said mould for replacing and resurfacing at least one of said carrying contacting surfaces of the knee joint.

According to one embodiment the method further comprises the step of the mould being melted by the injected material, and/or resorbed by the human body.

According to one embodiment the method further comprises the step of heating the material to a temperature of more than 40 degrees Celsius for transforming said material into a fluid, and the injected fluid material transforming to a fixed form when received in said mould.

According to another embodiment the method further comprises the step of heating the material to a temperature of more than 60 degrees Celsius for transforming said material into a fluid, and the injected fluid material transforming to a fixed form when received in said mould.

According to yet another embodiment the method further comprises the step of heating the material to a temperature of more than 90 degrees Celsius for transforming said material into a fluid, and the injected fluid material transforming to a fixed form when received in said mould.

According to yet another embodiment the method further comprises the step of heating the material to a temperature of more than 200 degrees Celsius for transforming said material into a fluid, and the injected fluid material transforming to a fixed form when received in said mould.

According to yet another embodiment the method further comprises the step of heating the material to a temperature of more than 60 degrees Celsius for transforming said material into a fluid, and the injected fluid material transforming to a fixed form when received in said mould.

According to one embodiment of the method, the mould is adapted to be introduced into the hip joint through a hole in the pelvic bone, according to another embodiment the mould is adapted to be introduced into the hip joint through a hole in the femoral bone and according to a third embodiment the mould is adapted to be introduced into the hip joint through a hole in the hip joint capsule.

According to another embodiment of the method, the mould is adapted to be introduced into the knee joint through a hole in the femoral bone, the tibia bone or knee joint capsule.

A third aspect is a method for resurfacing at least one carrying contacting surface of a hip joint of a human patient. The hip joint comprises an acetabulum and a caput femur. The method comprises the steps of: creating a hole passing into said hip joint, placing a mould between the acetabulum and the caput femur, and injecting material into the mould for resurfacing the carrying contacting surfaces of the hip joint.

The method could also be a method for treating hip joint osteoarthritis in a human patient by providing at least one hip joint surface. The hip joint comprising a caput femur and an acetabulum. The method comprising the steps of: cutting the skin of the human patient, dissecting an area of the pelvic bone on the opposite side from the acetabulum, creating a hole in the dissected area, the hole passing through the pelvic bone and into the hip joint of the human patient. Further, the method comprises the steps of: placing a mould between the acetabulum and the caput femur, and injecting material into the mould providing at least one hip joint surface.

According to a one embodiment the methods above could further comprise the step of the mould being resorbed by the human body.

In a different embodiment the mould is adapted to be melted by the material being heated.

A method for treating hip joint osteoarthritis in a human patient by providing at least one knee joint surface is further provided. The knee joint comprises a femoral bone and a tibia platform. The method comprises the steps of: cutting the skin of the human patient, dissecting an area of the femoral bone, creating a hole in the dissected area passing through the femoral bone and into the knee joint of the human patient, placing a mould between the femoral bone and the tibia platform, and injecting material into the mould providing at least one knee joint surface. The mould of the method could according to one embodiment be resorbable or adapted to melt by said material being heated.

A further method of treating hip joint osteoarthritis in a human patient by providing at least one knee joint surface is provided. The knee joint comprises a femoral bone and a tibia platform, the method comprising the steps of: cutting the skin of the human patient, creating a hole in the dissected area, the hole passing through the tibia bone and into the knee joint of the human patient, placing a mould between the femoral bone and the tibia platform, and injecting material into said mould providing at least one knee joint surface. The mould could be adapted to be resorbable or adapted to melt when heated.

A further method of treating hip joint osteoarthritis in a human patient is provided. The knee joint comprises a femoral bone and a tibia platform, the method comprising the steps of: cutting the skin of the human patient, creating a hole in said dissected area, said hole passing through the knee joint capsule and into the knee joint of the human patient, placing a mould between the femoral bone and the tibia platform, and injecting material into the mould providing at least one knee joint surface. The mould could be adapted to be resorbable or adapted to melt when heated.

A method for resurfacing at least one carrying contacting surface of a hip joint of a human patient, said hip joint comprising an acetabulum and a caput femur having contacting carrying surfaces carrying weight in the hip joint, the method comprising the steps of: inserting a needle or a tube like instrument into the patient's hip joint, using the needle or tube like instrument to fill the hip joint with a fluid, placing at least one arthroscopic camera and at least one instrument in the patient's hip joint, introducing a mould passing into the hip joint, placing a mould between the acetabulum and the caput femur, and injecting material into said mould for replacing and resurfacing at least one of said carrying contacting surfaces of the hip joint.

Furthermore a method of resurfacing at least one carrying contacting surface of a hip joint of a human patient is provided. The knee joint comprising the femoral bone and the tibia bone having contacting carrying surfaces carrying weight in the knee joint, the method comprising the steps of: inserting a needle or a tube like instrument into the patient's knee joint, using the needle or tube like instrument to fill the knee joint with a fluid, placing at least one arthroscopic camera and at least one instrument in the patient's knee joint, introducing a mould passing into the knee joint, placing a mould between the femoral bone and the tibia bone, and injecting material into the mould for replacing and resurfacing at least one of the carrying contacting surfaces of the knee joint.

A further method for resurfacing at least one carrying contacting surface of a knee joint of a human patient is provided. The knee joint comprising the femoral bone and the tibia bone having contacting carrying surfaces carrying weight in the knee joint, the method comprising the steps of: inserting a needle or a tube like instrument into the patient's knee joint, using the needle or tube like instrument to fill the knee joint with a gas, placing at least one arthroscopic camera and at least one surgical instrument in the patient's knee joint, dissecting an area of the tibia bone, creating a hole in the dissected area, the hole passing through the tibia bone and into the knee joint of the human patient, introducing a mould through said hole passing into the hip joint, placing the mould between the femoral bone and the tibia bone, and injecting material into the mould for providing at least one knee joint surface. The mould according to any of the embodiments herein could be adapted to be resorbable or adapted to melt when by the contact with the injected material.

The joint surface could comprise at least one artificial femoral surface or at least one artificial tibia surface. The medical device according to any of the embodiments could comprise at least one material selected from a group consisting of: polytetrafluoroethylene, perfluoroalkoxy and fluorinated ethylene propylene. It is furthermore conceivable that the material comprises a metal alloy, such as cobalt-chromium or titanium or stainless steel, or polyethylene, such as crosslinked polyethylene or gas sterilized polyethylene. The use of ceramic material is also conceivable, in the contacting surfaces or the entire medical device such as zirconium ceramics or alumina ceramics. According to one embodiment the medical device comprises a hydroxy-apatite coating.

In other embodiments the medical device could comprise fluoropolymer resins, Kevlar and/or acrylic polymer mixed with alumina trihydrate.

In any of the methods above the step of cutting the skin of said human patient could be performed in the abdominal wall of the human patient. The step of dissecting an area of the pelvic bone could comprises dissecting in at least one of the following areas: the abdominal cavity, an area between peritoneum and the pelvic bone, the pelvic area, and the inguinal area.

According to yet another embodiment, a method for treating hip joint osteoarthritis in a human patient by providing at least one hip joint surface is provided. The hip joint comprising a caput femur and an acetabulum. The method could comprise the steps of: cutting the skin of said human patient, creating a hole in the dissected area, the hole passes through the femoral bone and into the hip joint of the human patient. The method further comprises the steps of: placing a mould between the acetabulum and the caput femur, and injecting material into the mould providing at least one hip joint surface.

According to yet another embodiment, a method of treating hip joint osteoarthritis in a human patient by providing at least one hip joint surface is provided. The hip joint comprises a caput femur and an acetabulum. The method comprises the steps of: cutting the skin of said human patient, creating a hole in said dissected area, said hole passing through the hip joint capsule and into the hip joint of the human patient. Whereafter a mould is placed between said acetabulum and said caput femur, material is injected into said mould providing at least one hip joint surface.

According to yet another embodiment, a method for treating a hip joint of a human patient by providing at least one hip joint surface is provided. The hip joint comprises a caput femur and an acetabulum. The method comprises the steps of: inserting a needle or a tube like instrument into the patient's body, using the needle or tube like instrument to fill an area of the hip joint with gas thereby expanding a cavity, placing at least two laparoscopic trocars in the patient's body, inserting a camera through one of the laparoscopic trocars into the patient's abdomen, inserting at least one dissecting tool through one of the at least two laparoscopic trocars, dissecting an area of the pelvic bone on the opposite side from said acetabulum. Whereafter the method comprises the steps of: creating a hole in the dissected area, the hole passing through said pelvic bone and into said hip joint of said human patient, placing a mould between said acetabulum and said caput femur, and injecting material into said mould for providing at least one hip joint surface.

According to yet another embodiment a method for treating a hip joint of a human patient by providing at least one hip joint surface is provided. The hip joint comprises a caput femur and an acetabulum, the method comprises the steps of: inserting a needle or a tube like instrument into the patient's body, using the needle or tube like instrument to fill an area of the hip joint with gas thereby expanding a cavity, placing at least two laparoscopic trocars in the patient's body, inserting a camera through one of the laparoscopic trocars into the patient's body, inserting at least one dissecting tool through one of the at least two laparoscopic trocars, dissecting an area of the hip joint, creating a hole in the dissected area, said hole passing through the femoral bone and into the hip joint of the human patient, placing a mould between the acetabulum and the caput femur, and injecting material into the mould for providing at least one hip joint surface.

According to yet another embodiment a method for treating a hip joint of a human patient by providing at least one hip joint surface is provided. The hip joint comprises a caput femur and an acetabulum. The method comprises the steps of: inserting a needle or a tube like instrument into the patient's body, using the needle or tube like instrument to fill the patient's abdomen with gas thereby expanding a cavity, placing at least two laparoscopic trocars in the patient's body, inserting a camera through one of the laparoscopic trocars into the patient's abdomen, inserting at least one dissecting tool through one of the at least two laparoscopic trocars, dissecting an area of the hip joint, creating a hole in the dissected area, said hole passing through the hip joint capsule and into the hip joint of said human patient, placing a mould between said acetabulum and said caput femur, and injecting material into said mould for providing at least one hip joint surface.

The mould in any of the embodiments above could be adapted to be resorbable or adapted to melt after having served its purpose as mould.

Medical Device

A fourth aspect concerns a medical device for treating joint osteoarthritis by providing a joint surface. The medical device is made inside of the joint by injecting material into a mould.

According to one embodiment the medical device comprises at least one artificial hip joint surface, which could be at least one of an artificial caput femur surface and an artificial acetabulum surface.

According to one embodiment the medical device the joint surface comprises at least one artificial knee joint surface.

The medical device should serve as carrying contacting joint surface and for that purpose the medical device could comprise fluoropolymers, such as: polytetrafluoroethylene, perfluoroalkoxy and fluorinated ethylene propylene.

A method of treating hip joint osteoarthritis in a human patient by providing an artificial hip joint surface using a mould is further provided. The method comprises the steps of: the mould being placed inside of said hip joint, the mould being injected with a fluid adapted to harden, the fluid hardening inside of said hip joint, the mould being resorbed by the human body, and the hardened fluid serving as artificial hip joint surface.

A different embodiment of the method is a method of treating knee joint osteoarthritis in a human patient by providing an artificial knee joint surface using a mould. The method comprises the steps of: the mould being placed inside of said knee joint, the mould being injected with a fluid adapted to harden, the fluid hardening inside of said knee joint, the mould being resorbed by the human body, and the hardened fluid serving as artificial knee joint surface.

A method of creating the medical device according to any of the embodiments above using the mould according to any of the embodiments above is also provided.

According to one embodiment the fluid is adapted to be injected with such a high temperature to affect the nerve cells in the resurfacing contacting surface to damage the nerve cells to reduce pain.

Please note that any method or part of method may be combined with any other method or part of method to create any combination of methods or parts of methods.

BRIEF DESCRIPTION OF DRAWINGS

The embodiments are now described, by way of example, with reference to the accompanying drawings, in which:

FIG. 4a shows an anterior view of the knee joint,

FIG. 4b shows a side view of the knee joint,

FIG. 5 shows the creation of a large hole in the pelvic bone,

FIG. 6 shows the creation of a small hole in the pelvic bone,

FIG. 13 shows an arthroscopic camera being placed in a second hole in the pelvic bone, FIG. 14a shows an incision in the knee of a human patient, in an anterior view, FIG. 14b shows two laparoscopic incisions in the knee of a human patient, in an anterior view, FIG. 23 shows an instrument injecting a fluid into the mould in the hip joint, through the hip joint capsule, FIG. 24 shows the hip joint in section, after a fluid has been injected, FIG. 27a shows the knee joint when an injecting member injects a fluid into a mould, FIG. 27b shows the knee joint when an injecting member injects a fluid into a mould, in a laparoscopic embodiment.

DETAILED DESCRIPTION

Figure 1:
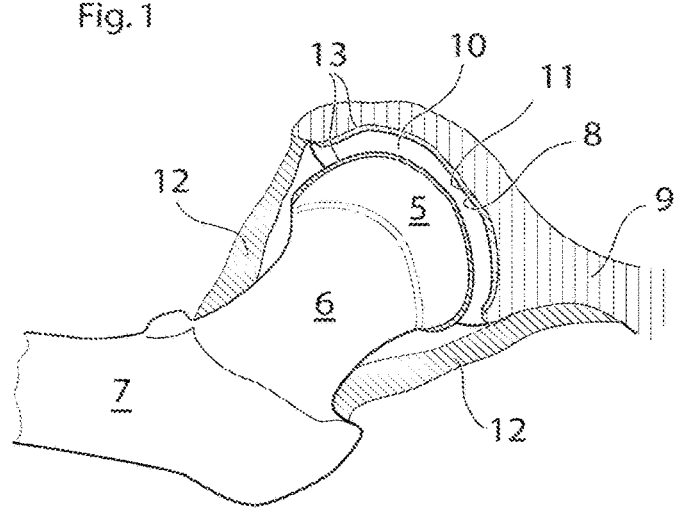
FIG. 1 shows the hip joint in section.

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In addition to the above, the following terms will be used:

Biocompatible material is to be understood as being a material with low level of immune response. Biocompatible materials are sometimes also referred to as biomaterials. Analogous is biocompatible metals a metal with low immune response such as titanium or tantalum. The biocompatible metal could also be a biocompatible alloy comprising at least one biocompatible metal.

Form fitting is to be understood as an element having a part or section which is adapted to enable a mechanical connection of said element to at least one other element using said part or section. Form fitted structure is a structure of an element which enables form fitting.

Elasticity is to be understood as a materials ability to deform in an elastic way.

Elastic deformation is when a material deforms under stress (e.g. external forces), but returns to its original shape when the stress is removed. A more elastic material is to be understood as a material having a lower modulus of elasticity. The elastic modulus of an object is defined as the slope of its stress-strain curve in the elastic deformation region. The elastic modulus is calculated as stress/strain, where stress is the force causing the deformation, divided by the area to which the force is applied; and strain is the ratio of the change caused by the stress.

Stiffness is to be understood as the resistance of an elastic body to deformation by an applied force.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements.

Functional hip joint is a hip joint that can perform functional hip movements either with or without an implanted medical device or prosthesis.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum or titanium or stainless steel, or polyethylene, such as cross-linked polyethylene or gas sterilized polyethylene. The use of ceramic material is also conceivable, in the contacting surfaces or the entire medical device such as zirconium ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

In the following a detailed description of embodiments will be given. In the drawing figures, like reference numerals designate identical or corresponding elements throughout the several figures. It will be appreciated that these figures are for illustration only and are not in any way restricting the scope. Thus, any references to direction, such as "up" or "down", are only referring to the directions shown in the figures. Also, any dimensions etc. shown in the figures are for illustration purposes.

FIG. 1 shows the hip joint of a human patient in section. The hip joint comprises a caput femur 5 placed at the very top of collum femur 6 which is the top part of the femur bone 7. The caput femur is in connection with the acetabulum 8 which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down or often down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 2:
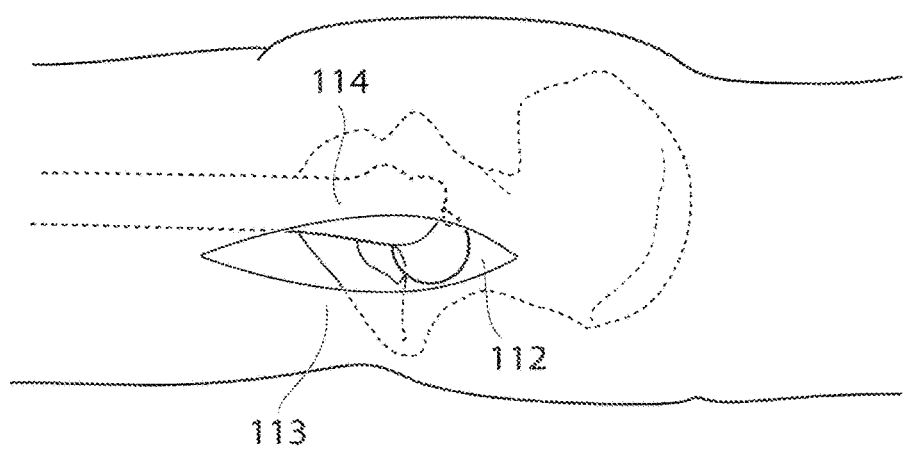
FIG. 2 shows a lateral view of a conventional hip joint surgery.

FIG. 2 shows a lateral view of a conventional hip joint surgery where an incision 112 is made in the tight 113 enabling the surgeon to reach the femur bone 7 on which the caput femur 5 is located. In a conventional hip joint surgery the hip joint is accessed through the hip joint capsule.

Figure 3:
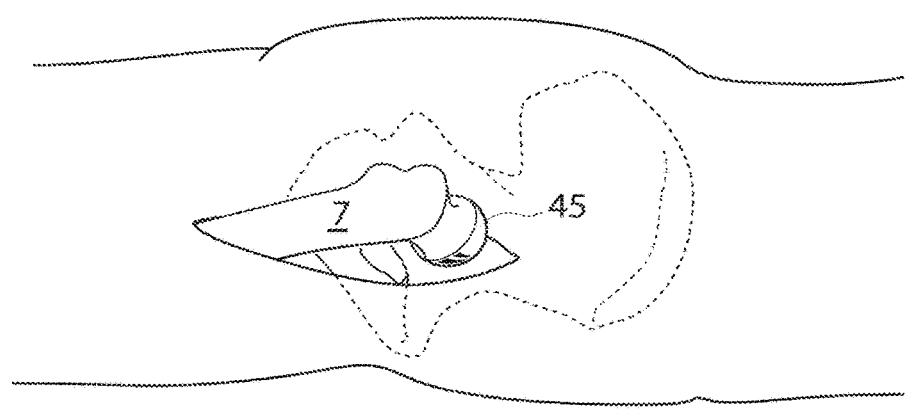
FIG. 3 shows a lateral view of a conventional hip joint surgery.

FIG. 3 shows the placing of an artificial caput femur surface 45 on the caput femur 5 in conventional surgery.

FIG. 4a shows the knee joint J of a left knee of a human in an anterior view. The lower extremity 211 of femur or the femoral bone 210 supplies the knee joint surface of the femoral bone, whereas the upper extremity of tibia 510 or the shinbone supplies the lower knee joint surface. The lower part of the leg comprises tibia 510 or the shinbone and fibula 511 or the calf bone. Furthermore FIG. 4 shows the knee joint when a resurfacing 213 of a knee joint J surface has been performed.

4b shows the knee joint in section from the side. The condyles 105 is the lower extremity of the femoral bone 210 and makes up the sides of the upper part of the knee joint. Tibia 510 or the shinbone constitutes the lower part of the knee joint, tibia is in connection with fibula 511 or the calf bone, tibia and fibula constitutes the bones of the lower part of the leg.

FIG. 5 shows an embodiment wherein the mould is to be used for resurfacing the hip joint. For placing the mould in the hip joint the hip joint needs to be reached, with reference to FIG. 1 this could be through a hole placed in the pelvic bone 9, the femoral bone 7 or the hip joint capsule 12. FIG. 5 shows the hole 18 in the pelvic bone 9 according to a first embodiment, the hole 18 is large which allows the mould to pass through said hole 18 in its full functional size.

FIG. 6 shows the hole 20 according to a second embodiment wherein the hole 20 created in a surgical or laparoscopic method is much smaller allowing the surgical instrument creating the hole to be smaller, and thus the incision and dissection performed in the human body. To place the mould in the joint in this embodiment the mould needs to be flexible or collapsible.

Figure 7:
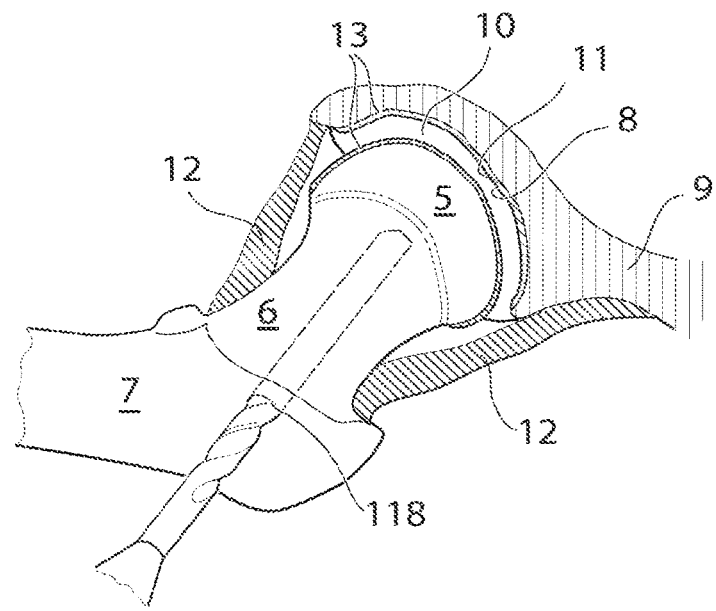
FIG. 7 shows the creation of a hole in the femoral bone.

FIG. 7 shows the hip joint in section when creating a hole in the femur bone 7. The hole in the femur bone passes through the caput femur 5 into the hip joint and enables the surgeon to reach the hip joint.

Figure 8:
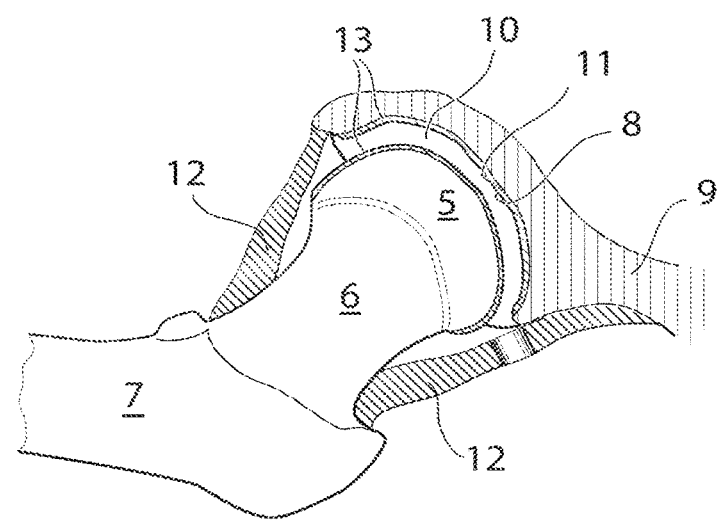
FIG. 8 shows the creation of a hole in the hip joint capsule.

FIG. 8 shows the hip joint in section when creating a hole in the hip joint capsule 12. The hole in the hip joint capsule passes into the hip joint and enables the surgeon to reach the hip joint.

Before the introduction of a mould or material into the hip joint the hip joint surfaces could need to be prepared. This preparation could be performed by reaming the acetabulum and/or the caput femur surface.

Figure 9:
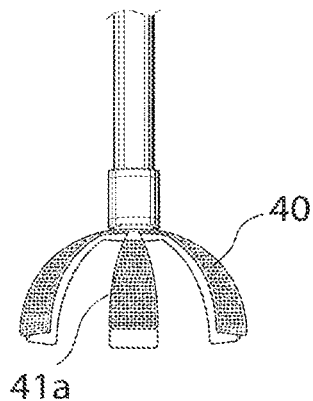
FIG. 9 shows an instrument adapted to ream, in a first state.

FIG. 9 shows a reamer according to a first embodiment wherein said reamer is expandable. The expandable reamer comprises at least one reaming blade 40 which comprises a reaming surface 41a,b. Said expandable reamer could be adapted to ream the acetabulum 8, the caput femur 5 or both. In the embodiment where said expandable reamer is adapted to ream the acetabulum 8 said reaming surface 41a is located on the exterior part of the at least one reaming blade 40, whereas in the embodiment when said expandable reamer is adapted to ream the caput femur 5, said reaming surface 41b is located on the interior part of the at least one reaming blade 40. According to a second embodiment said expandable reamer is adapted to ream both the acetabulum and the caput femur, in which case the reamer has reaming surfaces 41a,b both on the exterior and the interior part of the at least one reaming blade 40.

Figure 10:
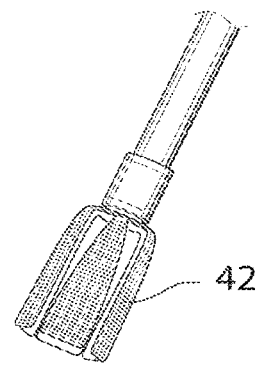
FIG. 10 shows an instrument adapted to ream, in a second state.

FIG. 10 shows the expandable reamer according to the first embodiment wherein the reaming blades 40 can be folded towards a center of the semi-sphere that the expandable reamer produces in its expanded state, shown in FIG. 15. The folding of the reaming blades 40 enables the expandable reamer to be introduced into a hip joint through a hole smaller than the area possible to ream using said expandable reamer.

Figure 11:
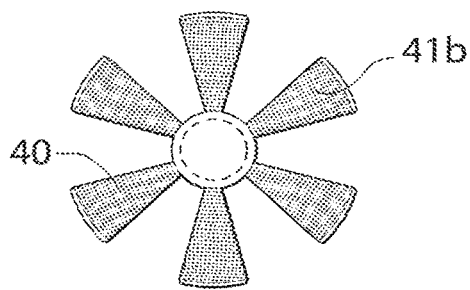
FIG. 11 shows an instrument adapted to ream, from underneath.

FIG. 11 shows the interior said of the expandable reamer with the reaming blades 40. In the embodiment when the expandable reamer is adapted to ream the caput femur said interior side of the at least one reaming blade 40 comprises a reaming surface 41b.

Figure 12:
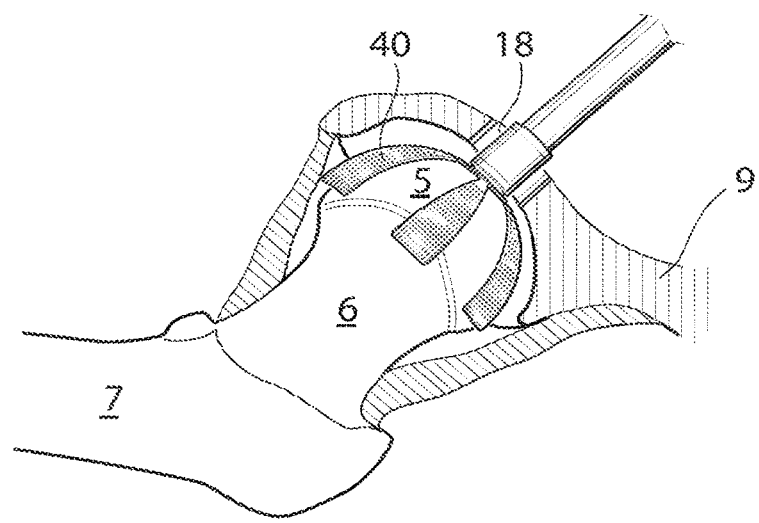
FIG. 12 shows an instrument adapted to ream, when reaming.

FIG. 12 shows the expandable reamer according to any of the embodiments when reaming said acetabulum 8 and/or said caput femur 5. The reamer can be adapted to be operated manually or by means of a rotating, vibrating or oscillating operating device.

To get a view inside the hip joint it is conceivable that the surgeon can make a second hole in the pelvic bone, the femoral bone or the hip joint capsule to insert a camera.

FIG. 13 shows the hip joint in section wherein a second hole 18b in the pelvic bone 9 enables the surgeon to place a camera 34 into the hip joint, preferably used in a laparoscopic method.

FIG. 14a shows the knee 214 in an anterior view and the creation of a hole passing into the knee joint J enabling the placing of a mould 81 inside of the knee joint J for resurfacing the knee joint surface of femur 210 or tibia 510.

FIG. 14b shows the knee 214 in an anterior view and the creation of a smaller hole for a laparoscopic/arthroscopic method, the hole passing into the knee joint J enabling the placing of a mould 81 inside of the knee joint J for resurfacing the knee joint surface of femur 210 or tibia 510.

After the preparation of the surfaces the mould needs to be inserted into either the hip joint or the knee joint.

Figure 15A:
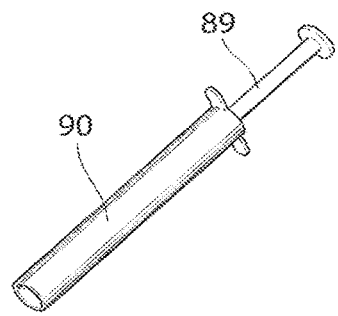
FIG. 15a shows an instrument for inserting a mould.

FIG. 15a shows an instrument for placing a mould 81 in the hip joint or the knee joint through a hole in the pelvic bone, the femur bone, the hip joint capsule or an area of the knee. The instrument comprises a piston 89 for transporting the mould 81 into the joint.

Figure 15B:
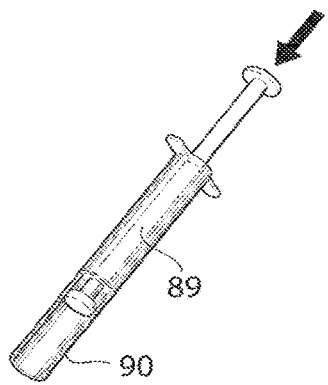
FIG. 15b shows an instrument for inserting a mould, in section.

FIG. 15b shows a section of the surgical instrument comprising a tube like element 90 for housing of said mould 81.

Figure 15C:
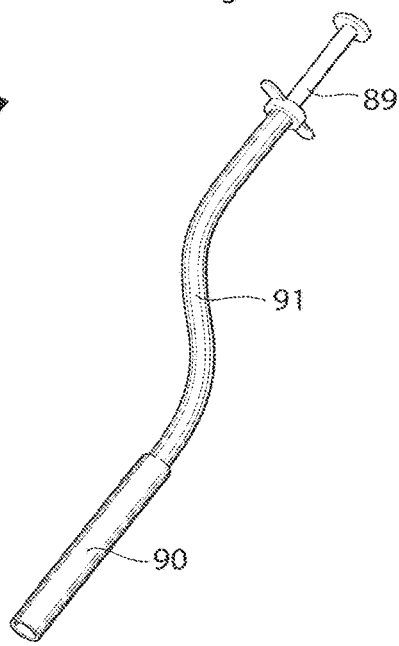
FIG. 15c shows an instrument for inserting a mould, comprising a flexible part or section.

FIG. 15c shows the surgical instrument according to another embodiment in which the surgical instrument comprises a flexible or bent part 91 improving the reach of the surgical instrument. The surgical instrument according to any of the embodiments can be used to place said mould 81 inside of a joint in any of the ways described in the following embodiments.

Figure 16A:
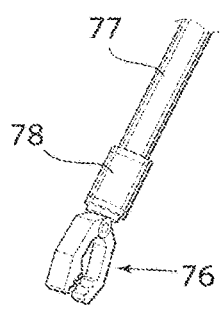
FIG. 16a shows an instrument for inserting a mould.

FIG. 16a shows an instrument adapted to insert the mould 81 in a hip joint or a knee joint, according to a second embodiment. According to this embodiment the surgical instrument comprises a gripping portion 76 and a handling portion 77. According to the embodiments shown in FIG. 14a,b,c the instrument further comprises a rotation element 78 that enables the gripping part 76 to rotate in relation to the handling part 77, however it is equally conceivable that the surgical instrument lacks this rotation element 78.

Figure 16B:
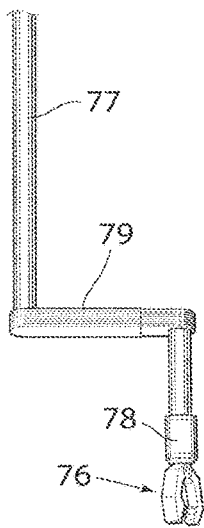
FIG. 16b shows an instrument for inserting a mould, comprising a parallel displaced part or section.

FIG. 16b shows the surgical instrument adapted to insert the mould 81 in a hip joint or a knee joint, according to a third embodiment. According to this embodiment the surgical instrument further comprises a parallel displaced section 79, which increases the reach of the instrument and facilitates the reaching of the hip joint through a hole in the pelvic bone, the femoral bone or the hip joint capsule.

Figure 16C:
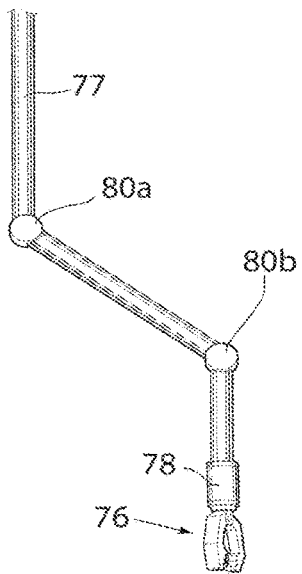
FIG. 16c shows an instrument for inserting a mould, comprising two joints.

FIG. 16c shows the surgical instrument adapted to insert the mould 81 in a hip joint, according to a third embodiment. According to this embodiment the surgical instrument further comprises two angle adjusting members 80a, b. The angle adjusting members could be adjustable for varying the angle of said gripping part 76 in relation to the handling portion 77, or fixed in an angle suitable for operating in a joint through a hole in the pelvic bone, the femur bone, the hip joint capsule or an area of the knee joint.

FIGS. 17-24 shows the insertion and use of a mould produced from a biologically resorbable polymer film. Said mould is made to fit into the acetabular fossa and to define the shape of an acetabular cup. The mould is sterilized and evacuated.

The sterile mould is inserted in a hip joint, and a liquid polymer mixture is injected into said mould, filling said mould, whereby said mold in its filled state takes the shape of an acetabular cup. The polymer mixture is cured in said mould, and retains the shape defined by said mould, whereupon said polymer film forming the mould is resorbed, leaving a cured polymer solid in the shape of an acetabular cup.

The biologically resorbable film is chosen from films and membranes made of polylactide polymers, polyglycolide polymers, polycaprolactone polymers, or lactide/glycolide copolymers, or lactide/caprolactone cellulose-based film; a hyaluronan-based film, a fibrin-based film, a collagen-based film, a chitosan-based film or combinations thereof.

A non-limiting example of a bioabsorbable membrane is the Cytoskin™ membrane (Biogeneral Inc., San Diego, Calif., USA) available in a thickness of 12 μm to 150 μm. Other bioabsorbable materials are exemplified by the Purasorb® product line (Purac Biomaterials, Gorinchem, The Netherlands). The Purasorb® materials can be processed by conventional processing techniques, such as extrusion, compression molding and injection molding, and can be subjected to different sterilization techniques. These materials are commercially available in the form of various resorbable orthopedic implant devices. With the advantages of excellent biocompatibility and biodegradability they serve as the matrix in a wide variety of applications to treat injuries of the muscoskeletal system in areas such as sports medicine, trauma and spinal surgery. Further, the properties of the Purasorb® polymers can be tailored to the application to meet all the design criteria.

Clinical experience in a large number of cases shows that a lactic acid-glycolic acid copolymer is resorbed in 12-15 months in craniosynostosis surgery. It is very likely that the resorption time in a joint would be shorter, as the film will be subject to mechanical wear.

The liquid polymer mixture is chosen from polytetrafluoroethylene, perfluoroalkoxy propylene, fluorinated ethylene propylene, polyethylene, and highly crosslinked polyethylene.

Another example of embodiment is a resorbable mould with accelerated resporption. The biological resorption of the mould is accelerated by the introduction of an agent taking part in, or accelerating, the resorption. When the film for example comprises a hyaluronan-based material, hyaluronidase can be added in a suitable amount, when the film comprises a fibrin-based material, plasmin is added in a suitable amount, when the film comprises a collagen-based material, collagenase is added in a suitable amount, and when the film comprises a chitosan-based material, lysozyme is added in a suitable amount.

Another example of embodiment is a resorbable mould with inner coating. As in the previous embodiments the mould is produced from a biologically resorbable polymer film, for example but not limited to the Cytoskin™ membrane (Biogeneral Inc.). The inside of the mould is coated with a biocompatible compound which improves the properties of the acetabular cup, for example reduced friction, increases surface strength, reduces wear etc. A non-limiting example of such coating is a biocompatible phospholipid polymer, 2-methacryloyloxyethyl phosphorylcholine (MPC) shown to form a hydrated lubricating layer, significantly decreasing friction and wear, reducing the amount of wear particles compared to uncoated joint surfaces.

When the mould is filled with the polymer mixture intended to form the acetabular cup, the MPC-coating will be grafted into the outer surface of the solid polymer, significantly reducing friction and wear. The mould itself will be resorbed through the action of natural resorption mechanisms, or resorption mechanisms augmented through the addition of suitable agents, as described above, exposing the coated surface.

Another example of embodiment is a mould that melts and integrates with core. In order to form an acetabular cup inside a hip joint, using a polymer mixture, e.g. a polymer having a melting point in the interval 40-60° C., or 40-90° C., or 40-200° C., or 40 to 400° C., a mould is produced from a polymer film, said polymer chosen from polymers having the same or lower melting point as said polymer.

Said mould is shaped to fit into the acetabular fossa and to define the shape and volume of an acetabular cup. The mould is sterilized and evacuated.

The mould is inserted in a hip joint, and a heated liquid polymer mixture is introduced e.g. injected into said mould, the temperature of the liquid polymer mixture being above both the melting point of the polymer mixture, and above the melting point of the polymer forming the mould. When filling said mould, the heated polymer contacts and melts the film forming the mould, and seamlessly integrates with said film.

Another example of embodiment is a mould that melts and is absorbed by core. An alternative to the examples described above is that the biocompatible material forming the mould, and the polymer material forming the core of the artificial acetabular cup, are chosen so that the material forming the mould will be resorbed by the material forming the core. In order to achieve this, a skilled person will need to study the melting temperature of the materials, the surface properties, charge and other properties of the materials. The material forming the mould and the material forming the core are chosen so that the material forming the mould will be absorbed by the core material.

Figure 17:
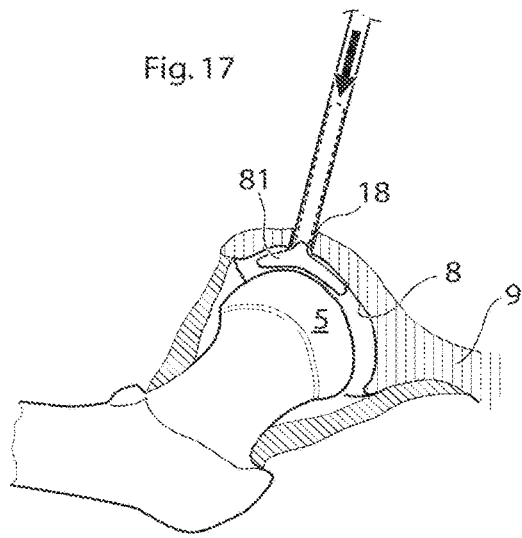
FIG. 17 shows the placing of a mould in the hip joint through the pelvic bone.
Figure 18:
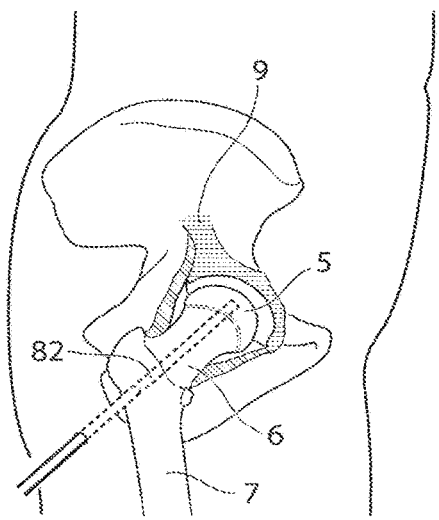
FIG. 18a shows the placing of a mould in the hip joint through the femoral bone.
FIG. 18b shows the placing of a mould in the hip joint through the femoral bone.
FIG. 18c shows the placing of a mould in the hip joint through the femoral bone.
FIG. 18d shows the mould in place in the hip joint.
Figure 18:
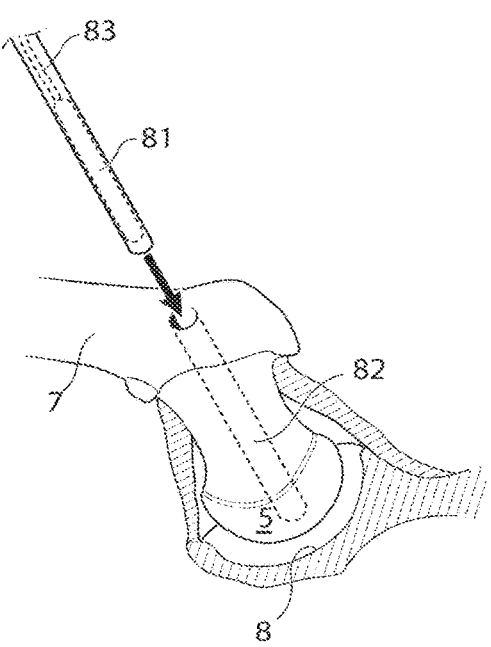
Figure 18:
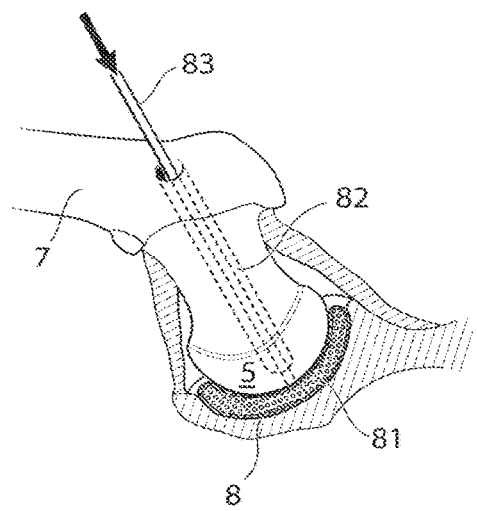
Figure 18:
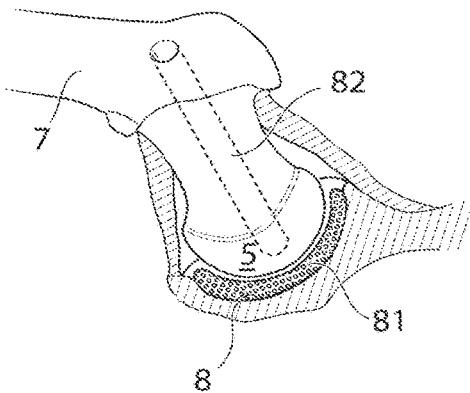

FIG. 17 shows the step of placing the mould 81 inside of the hip joint of a human patient through a hole 18 in the pelvic bone 9. The step of placing said mould 81 can be performed in a surgical, or in a laparoscopic/arthroscopic method.

FIG. 18a,b,c,d shows an alternative approach to placing said mould 81 in the hip joint of a human patient. Said alternative approach comprises the steps of creating a hole 82 in the femur bone 7 following a length axis of the collum femur 6, said hole starting from the lateral side of the thigh, penetrating the cortex of the femur bone 7 and eventually reaching the cortex of the caput femur 5 from the inside thereof, penetrating said cortex and entering into the hip joint. After the creation of the hole 82 in the femur bone 7 the mould 81 is inserted into the hip joint through the hole 82 using the surgical instrument 83 according to any of the embodiments above, as shown in FIG. 18b.

FIG. 18c shows the mould 81 when being inserted into the hip joint using the surgical instrument 83 adapted therefore.

FIG. 18d shows the mould 81 in place after insertion into the hip joint, the surgical instrument used to place said mould 81 in the hip joint is retracted after the insertion is completed.

Figure 19:
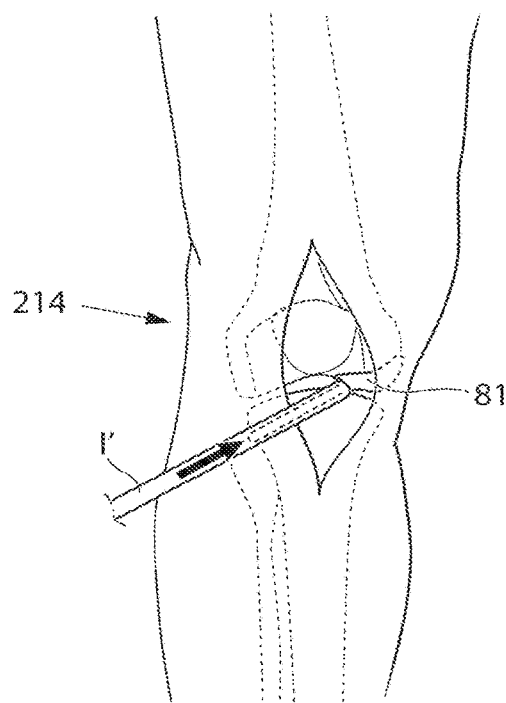
FIG. 19 shows the placing of a mould in the knee joint.

FIG. 19 shows the placing of a mould 81 in a knee 214 in a surgical method. The mould 81 is placed using the surgical instrument according to any of the embodiments above.

Figure 20:
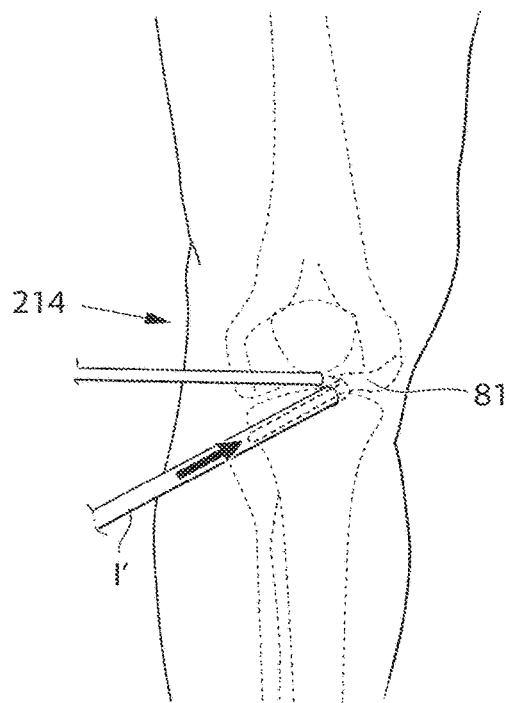
FIG. 20 shows an instrument injecting a fluid into the mould in the knee joint.

FIG. 20 shows the placing of a mould 81 in a knee 214 in a laparoscopic method. The mould 81 is placed using the surgical instrument according to any of the embodiments above.

After the mould has been placed in the hip or knee joint it is filled with a fluid adapted to harden to a medical device adapted to serve as at least one artificial joint surface.

Figure 21:
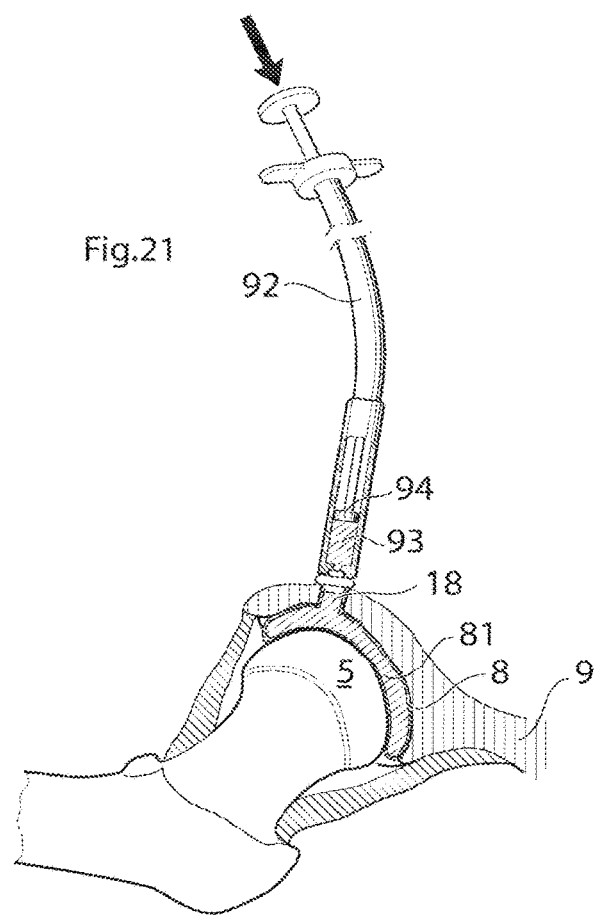
FIG. 21 shows an instrument injecting a fluid into the mould in the hip joint, through the pelvic bone.

FIG. 21 shows the hip joint in section wherein an injecting member 92 injects a fluid 93 into a mould 81 in the hip joint through a hole 18 in the pelvic bone 9 from the opposite side from acetabulum 8. The injecting member 92 comprises a piston 94 that pushes said fluid 93 into the mould 81.

Figure 22:
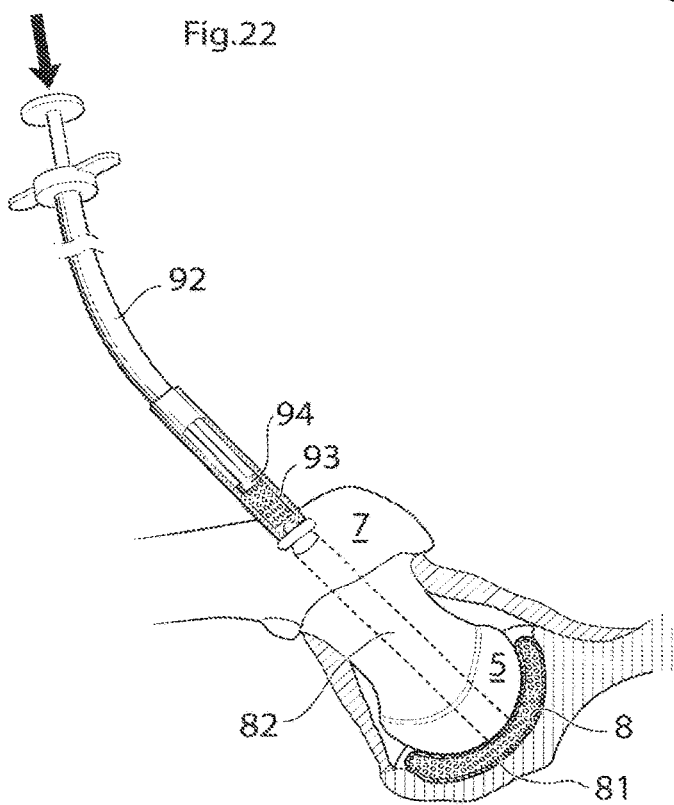
FIG. 22 shows an instrument injecting a fluid into the mould in the hip joint, through the femoral bone.

FIG. 22 shows the hip joint in section wherein an injecting member 92 injects a fluid 93 into a mould 81 in the hip joint through a hole 82 in the femur bone 7. The injecting member 92 comprises a piston 94 that pushes said fluid 93 into the mould 81.

FIG. 23 shows the hip joint in section wherein an injecting member injects a fluid 93 into a mould 81 in the hip joint through a hole in the hip joint capsule 12. The injecting member 92 comprises a piston 94 that pushes said fluid 93 into the mould 81. Said fluid 93 being adapted to harden to create a medical device adapted to serve as at least one artificial hip joint surface.

FIG. 24 shows the hip joint in section wherein the medical device 93' is located between the acetabulum 8 and the caput femur 5 which has been created by the hardening of the fluid 93 adapted to harden. Said medical device is adapted to serve as at least one artificial hip joint surface. The hole in the pelvic bone is preferably sealed with a bone plug 31 or a prosthetic part 98. The mould 81 used to create the medical device 93' has been resorbed by the human body. According to another embodiment the mould used to create the medical device 93' has melted.

Figure 25:
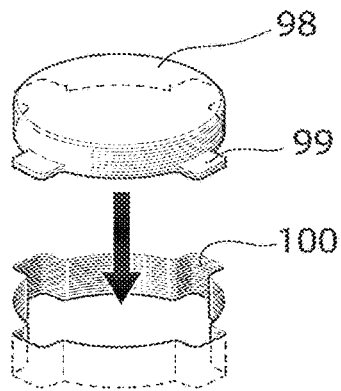
FIG. 25a shows a prosthetic part being used to close a hole in a pelvic bone.
FIG. 25b shows how sections of a prosthetic part is used as support against the edges of the hole in a pelvic bone.
FIG. 25c shows the insertion of a prosthetic part in a hole in a pelvic bone.
Figure 25:
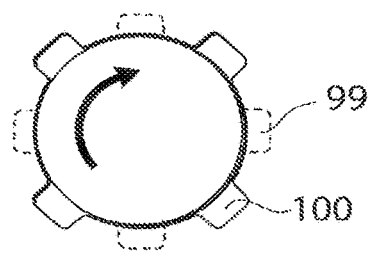
Figure 25:
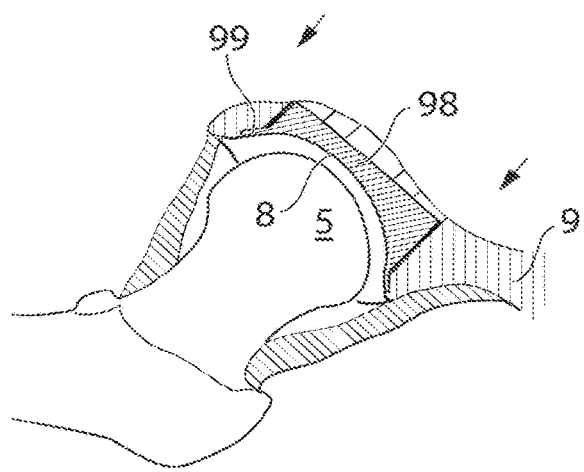

FIG. 25a shows the prosthetic part 98 being inserted into a hole 18 in the pelvic bone 9 from the opposite side from acetabulum 8. According to one embodiment the prosthetic part 98 comprises supporting members 99 adapted to correspond with sections 100 of the hole 18 in the pelvic bone 9. After the prosthetic part 98 has been inserted into said hole 18 in the pelvic bone 9 it is rotated so that the supporting members 99 comes in contact with the pelvic bone 9 and can carry the load placed on the acetabulum 8 from weight of the human patient through the contact with the caput femur 5. Said prosthetic part 98 could also be adapted to serve as artificial acetabulum surface 65 according to any of the above mentioned embodiments.

FIG. 25b shows the prosthetic part 98 when rotated to carry the load placed on the acetabulum 8 from weight of the human patient through the contact with the caput femur 5.

FIG. 25c shows the hip joint of a human patient in section wherein the prosthetic part 98 closes the hole 18 in the pelvic bone 9 and carries the load placed on the acetabulum 8 from weight of the human patient through the contact with the caput femur 5 by means of the supporting members 99. The prosthetic part 98 can further be fixated to the pelvic bone 9 by means of bone cement, adhesive, screws, form fitting, welding, sprints, band or some other mechanical connecting member.

Figure 26:
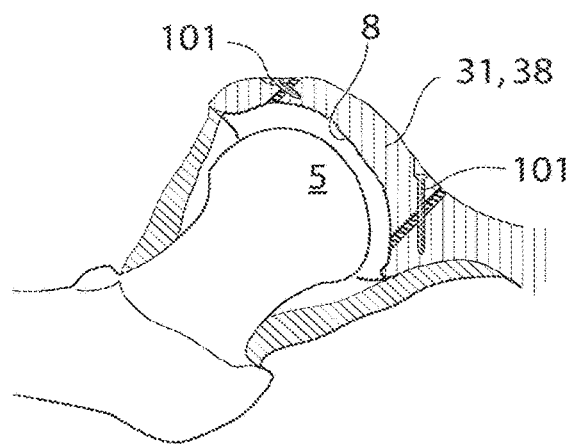
FIG. 26a shows how screws are being used to fixate a bone plug or a prosthetic part in a hole in a pelvic bone of a human patient.
FIG. 26b shows the hip joint in section when fixation elements are placed.
FIG. 26c shows the hip joint in section when fixation elements are placed.
FIG. 26d shows the hip joint in section when fixation elements are placed.

FIG. 26a shows the hip joint of a human patient in section wherein bone plug 31 or prosthetic part 98 is attached to the pelvic bone 9 by means of screws 101 placed from the opposite side from acetabulum 8. The screws 101 are possible to place in different angles depending on reach or need for support.

FIG. 26b shows the hip joint of a human patient in section wherein bone plug 31 or prosthetic part 98 is attached to the pelvic bone 9 by means of a plate 102 at least partly covering said bone plug 31 or prosthetic part 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member.

FIG. 26c shows the hip joint of a human patient in section wherein two bone plugs 31 or prosthetic parts 98 are attached to the pelvic bone 9 by means of a plate 102 at least partly covering said bone plugs 31 or prosthetic parts 98. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member.

FIG. 26d shows the hip joint of a human patient in section wherein two holes 18 in the pelvic bone has been covered by means of a fluid injected into said holes 18, through sealing members 104, said fluid 93 being adapted to harden. Further more a plate 102 has been provided at least partly covering said holes 18. According to a first embodiment the plate 102 is attached to the pelvic bone 9 by means of screws 103 placed from the opposite side from acetabulum 8. However it is also conceivable that said screws 103 can be replaced or assisted by bone cement, adhesive, form fitting, welding, sprints, band or some other mechanical connecting member. FIG. 66d also shows the provided artificial acetabulum surface 65, and the provided artificial caput femur surface 45.

FIG. 27a shows the knee joint wherein an injecting member 92 injects a fluid 93 into a mould 81 in the knee joint. The injecting member 92 comprises a piston 94 that pushes said fluid 93 into the mould 81. Said fluid 93 being adapted to harden to create a medical device adapted to serve as at least one artificial knee joint surface.

FIG. 27b shows the knee joint wherein an injecting member 92 injects a fluid 93 into a mould 81 in the knee joint through a small hole 18' in a laparoscopic/arthroscopic method. The injecting member 92 comprises a piston 94 that pushes said fluid 93 into the mould 81. Said fluid 93 being adapted to harden to create a medical device adapted to serve as at least one artificial knee joint surface.

Figure 28:
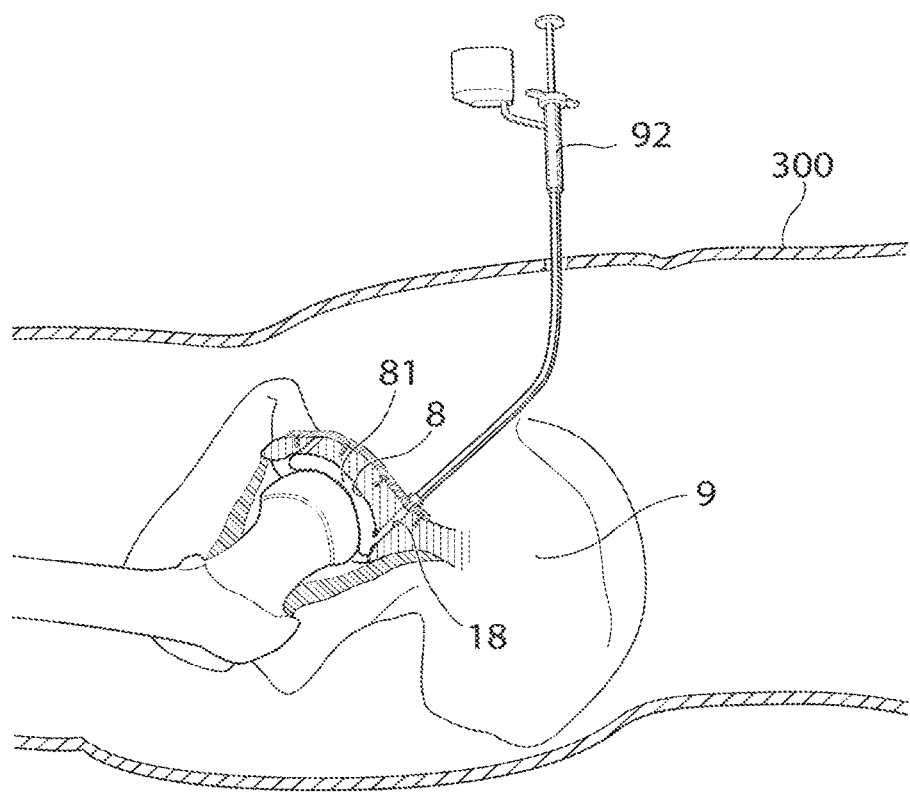
FIG. 28 shows a human patient in a lateral view when an injecting member injects a fluid into a mould.

FIG. 28 shows a lateral section of the human body wherein an injecting member 92 injects a fluid into a mould 81 in the hip joint through a hole 18 in the pelvic bone 9 from the opposite side from acetabulum 8. The injecting member penetrating the skin 300 of the human patient in a surgical or laparoscopic method.

Figure 29:
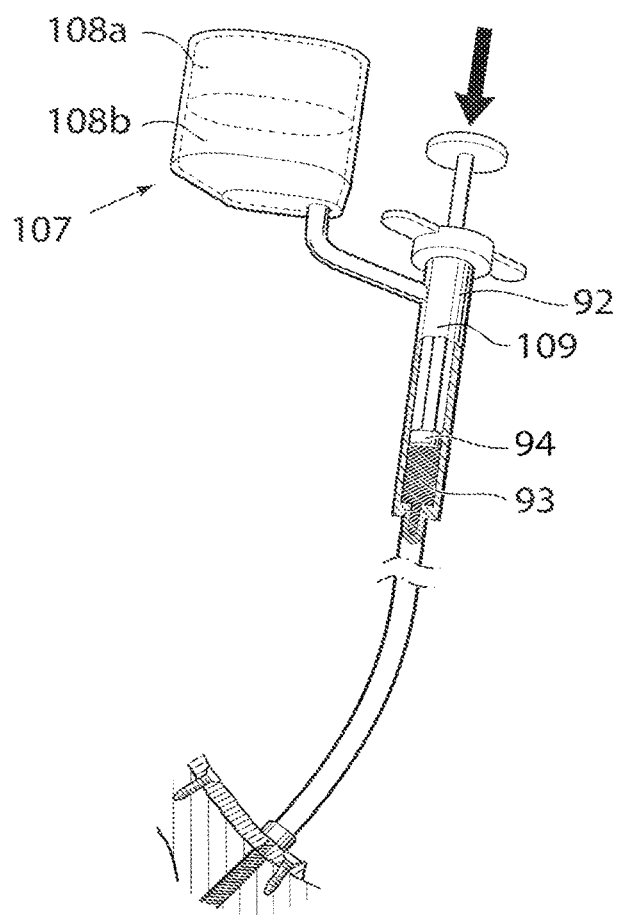
FIG. 29 shows an injecting member in further detail.

FIG. 29 shows the injecting member 92 according to any of the embodiments above, adapted to inject fluid 93 into a mould 81 in the hip joint or the knee joint. The injecting member 92 could further be adapted to inject material 93 or a fluid 93 into a connecting area between the pelvic bone 9 and a prosthetic part, the pelvic bone 9 and a bone plug 31 or the caput femur 5 and a prosthetic part. Said injecting member 92 comprises a container 107 adapted to hold a fluid 93 for injection. According to a first embodiment said container 107 comprises two compartments 108a,b adapted to hold two different fluids, said fluids being adapted to harden when mixed. In the embodiment when the container 107 is adapted to hold two fluids, it is conceivable that the injecting member 105 further comprises a mixing member 109 wherein said two fluids are being mixed before injection. According to a second embodiment (not shown) said container 107 is adapted to keep said fluid sterile. According to a third embodiment (not shown) said container 107 is adapted to keep said fluid cold or hot and according to a fourth embodiment (not shown) said container 107 is adapted to keep said fluid in a dark environment. Furthermore a combination of the above mentioned embodiments is conceivable.

According to another embodiment (not shown) the fluid is adapted to harden through the mixing with a gas. In which case one of the two compartments is adapted to hold a pressurized gas (such as nitrogen gas) adapted to act as catalyzing agent for the fluid adapted to harden. According to that embodiment the mixing unit 109 is adapted to mix one liquid and one gas fluid. Said first, second or mixed fluid could also be adapted to harden by means of UV-light, thermal change or contact with a body fluid.

Figure 30:
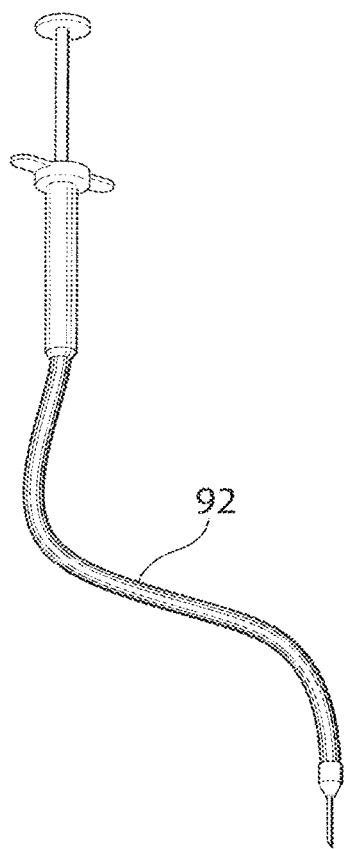
FIG. 30 shows an injecting member, comprising a flexible part or section.
Figure 31:
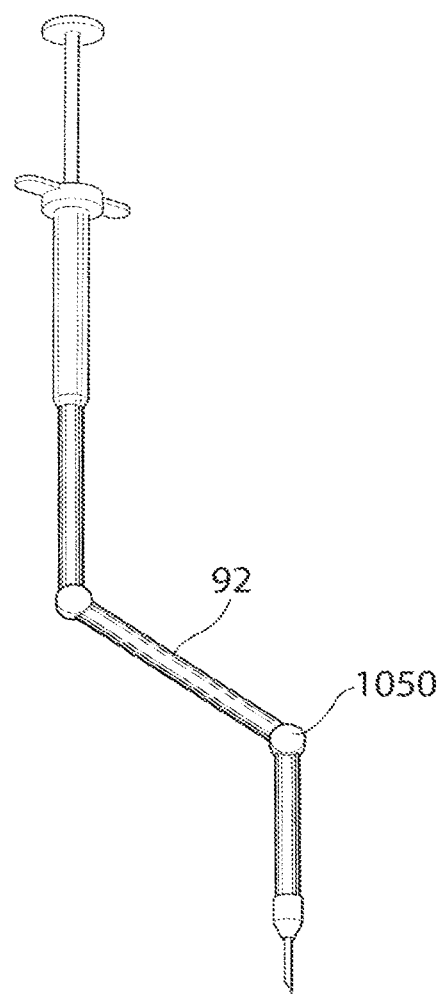
FIG. 31 shows an injecting member, comprising two joints.

FIG. 30 shows an injecting member 92 wherein the injecting member comprises a part or section adapted to bend. The instrument could be adapted to bend by means of said injecting member being flexible, shown in FIG. 30, or comprising at least one joint, shown in FIG. 31.

Please note that any embodiment or part of embodiment as well as any method or part of method could be combined in any way. All examples herein should be seen as part of the general description and therefore possible to combine in any way in general terms.

The invention claimed is:

1. A surgical or arthroscopic method for providing an artificial joint surface in a human patient using a mold, said method comprising the steps of:
    placing at least two trocars in an area of the patient being located in the proximity of a bone adjacent to a joint,
    inserting a camera through one of the trocars,
    inserting at least one dissecting tool through one of said at least two trocars,
    dissecting an area of the adjacent bone,
    creating a hole in said dissected area, said hole passing through the adjacent bone and into the joint of the human patient,
    placing said mold inside of the joint,
    injecting said mold with a fluid adapted to cure, wherein said mold is adapted to chemically react with the injected fluid such that said mold is resorbed by the human body and/or melts by the injected material,
    wherein the step of placing said mold inside of the joint is conducted by introducing a mold passing through the hole into the joint, and thereafter conducting the step of injecting said mold with a fluid adapted to cure, also through said hole, and said fluid being adapted to cure serving as artificial joint surface.

2. The surgical or arthroscopic method according to claim 1, wherein said mold comprises a material adapted to chemically react with the injected fluid material such that said mold melts or is resorbed by the human body after having received the injected fluid material and thus served its purpose.

3. The surgical or arthroscopic method according to any one of claims 1 or 2, wherein after said fluid has cured inside of the joint said fluid serves as an artificial joint surface.

4. The method according to any one of claims 1 or 2, wherein said method further comprises the step of heating said fluid to a temperature of more than 40 degrees Celsius for transforming said fluid from a solid to a fluid, and said injected fluid transforming to a solid when received in said mold, or heating said fluid to a temperature of more than 60 degrees Celsius for transforming said fluid from a solid to a fluid, and said injected fluid transforming to a solid when received in said mold, or heating said fluid to a temperature of more than 90 degrees Celsius for transforming said fluid from a solid to a fluid, and said injected fluid transforming to a solid when received in said mold, or heating said material to a temperature of more than 200 degrees Celsius for transforming said material into a fluid, or heating said fluid to a temperature of more than 400 degrees Celsius for transforming said fluid from a solid to a fluid, and said injected fluid transforming to a solid when received in said mold.

5. The method according to claim 4, wherein said fluid is injected with such a high temperature that it affects the nerve cells in a resurfacing contacting surface to damage the nerve cells to reduce pain.

6. The method according to any one of claims 1 or 2 further comprising the step of:
inserting a needle or a tube like instrument into a cavity of the patient being located in the proximity of a bone adjacent to said joint,
using the needle or tube like instrument to fill the cavity with a gas,
wherein the at least two trocars are laparoscopic trocars.

7. The method according to claim 1 or 2, wherein said joint in a human patient is one of a shoulder joint, an elbow joint, a hip joint, a knee joint or a foot joint.

8. The method according to claim 7, wherein, if the said joint is a hip joint the step of placing said mold into the hip joint comprises the step of introducing said mold through a hole in the pelvic bone or a hole in the femoral bone or a hole in the hip joint capsule, and if said joint instead is the knee joint the step of placing said mold into the knee joint comprises the step of introducing said mold through a hole in the femoral bone or a hole in the tibia bone or a hole in the knee joint capsule.

9. The method according to claim 6, wherein the joint is a knee joint, the knee joint comprising the femoral bone and the tibia bone having contacting carrying surfaces carrying weight in the knee joint, the method steps comprise:
inserting said needle or said tube like instrument into the patient's knee joint,
using the needle or tube like instrument to fill the knee joint with a gas,
placing said at least one arthroscopic camera and said at least one surgical instrument in the patient's knee joint,
dissecting an area of the tibia bone,
creating a hole in said dissected area, said hole passing through the tibia bone and into the knee joint of the human patient,
introducing a mold through said hole passing into the knee joint,
placing said mold between the femoral bone and the tibia bone,
said fluid curing inside of the knee joint and serving as artificial knee joint surface.

10. The method according to claim 6, wherein the joint is a hip joint of a human patient, the hip joint comprising an acetabulum and a caput femur having contacting carrying surfaces carrying weight in the hip joint, the method steps comprise:
inserting said needle or said tube like instrument into the patient's abdomen,
using the needle or tube like instrument to fill the abdomen with a gas,
placing at least two laparoscopic trocars in the patient's abdomen,
inserting a camera through one of the laparoscopic trocars into the patient's abdomen,
inserting at least one dissecting tool through one of said at least two laparoscopic trocars,
dissecting an area of the pelvic bone on the opposite side from the acetabulum,
creating a hole in said dissected area, said hole passing through the pelvic bone and into the hip joint of the human patient,
introducing a mold passing into the hip joint,
placing said mold between the acetabulum and the caput femur,
said fluid curing inside of the hip joint and serving as artificial hip joint surface.

11. The method according to claim 10, wherein the step of dissecting an area of the pelvic bone comprises dissecting in at least one of the following areas:
the abdominal cavity,
an area between peritoneum and the pelvic bone,
the pelvic area, and
the inguinal area.

12. The method according to any one of claims 1 or 2, wherein said mold comprises an activation material chosen from one of
a hyaluronan-based material,
a fibrin-based material,
a collagen-based material,
a chitosan-based material.

13. The method according to claim 12, wherein said fluid adapted to cure comprise
hyaluronidase if said mold's activation material is hyaluronan-based material,
plasmin if said mold's activation material is fibrin-based material,
collagenase if said mold's activation material is collagen-based material,
lysozyme if said mold's activation material is chitosan-based material,
wherein the material of said mold is affected by the injection of the fluid adapted to cure such that the mold melts or is resorbed faster than without the injection of the corresponding fluid adapted to cure.

* * * * *